United States Patent
Willey et al.

(10) Patent No.: US 10,342,706 B2
(45) Date of Patent: Jul. 9, 2019

(54) ELECTROCHEMICAL GASOTRANSMITTER GENERATING COMPOSITIONS AND METHODS OF USING SAME AND DRESSINGS AND TREATMENT SYSTEMS INCORPORATING SAME

(71) Applicant: Noxsano Inc., Columbus, OH (US)

(72) Inventors: Alan Willey, Cincinnati, OH (US); Stevan Samuel, Cincinnati, OH (US)

(73) Assignee: Noxsano Inc., Columbus, OH (US)

(*) Notice: Subject to any disclaimer, the term of this patent is extended or adjusted under 35 U.S.C. 154(b) by 0 days.

(21) Appl. No.: 15/874,665

(22) Filed: Jan. 18, 2018

(65) Prior Publication Data

US 2018/0221210 A1 Aug. 9, 2018

Related U.S. Application Data

(60) Provisional application No. 62/457,039, filed on Feb. 9, 2017.

(51) Int. Cl.
*A61F 13/00* (2006.01)
*A61K 33/04* (2006.01)
(Continued)

(52) U.S. Cl.
CPC ........ *A61F 13/00008* (2013.01); *A61K 33/04* (2013.01); *A61L 2300/102* (2013.01); *C01B 17/48* (2013.01); *C01B 21/50* (2013.01)

(58) Field of Classification Search
CPC ............... A61F 13/00008; A61L 2300/102
See application file for complete search history.

(56) References Cited

U.S. PATENT DOCUMENTS 5,797,887 A * 8/1998 Rosen ............... A61L 29/085
424/425
5,994,444 A * 11/1999 Trescony ............ A61L 29/085
524/429

(Continued)

FOREIGN PATENT DOCUMENTS

BR 102013022095-7 A2 8/2016

OTHER PUBLICATIONS

Thromboresistant/Anti-Biofilm Catheters via Electrochemically Modulated Nitric Oxide Release. Ren et al. Bioelectrochemistry. Aug. 2015; 104: 10-16.*

(Continued)

*Primary Examiner* — Bhisma Mehta
*Assistant Examiner* — Matthew A Engel
(74) *Attorney, Agent, or Firm* — Taft Stettinius & Hollister LLP

(57) ABSTRACT

Disclosed are compositions that comprise an organic electrochemical mediator and a gasotransmitter salt which converts into a gasotransmitter via electron transfer. Also disclosed are bandages and wound dressings comprising the subject gasotransmitters, and methods of making a gasotransmitters, comprising exposing the compositions to a voltage sufficient to reduce the water soluble organic mediator. Further disclosed are methods of treating a variety of trauma and disease states by applying a therapeutically effective amount of at least one gasotransmitter thereto, and methods of generating an effective dose of the gasotransmitter generated from electrolytic reaction involving the gasotransmitter-generating compositions.

21 Claims, 6 Drawing Sheets

(51) Int. Cl.
  *C01B 17/48* (2006.01)
  *C01B 21/50* (2006.01)

(56) References Cited

U.S. PATENT DOCUMENTS

| | | | |
|---|---|---|---|
| 6,103,275 A * | 8/2000 | Seitz | A61K 9/0014 |
| | | | 424/718 |
| 8,771,755 B2 | 7/2014 | Gojon-Romanillos et al. | |
| 9,480,785 B2 | 11/2016 | Meyerhoff et al. | |
| 2009/0036516 A1 * | 2/2009 | Scherrer | C07C 279/12 |
| | | | 514/441 |
| 2012/0296266 A1 * | 11/2012 | Malinski | A61M 13/003 |
| | | | 604/24 |
| 2017/0105879 A1 * | 4/2017 | Scholz | A61F 13/00063 |

OTHER PUBLICATIONS

Electrochemically Modulated Nitric Oxide (NO) Releasing Biomedical Devices via Copper(II)-Tri(2-pyridylmethyl)amine Mediated Reduction of Nitrite. Ren et al. ACS Appl. Mater. Interfaces. 2014; 6: 3779-3783.*

A novel method for the delivery of nitric oxide therapy to the skin of human subjects using a semi-permeable membrane. Hardwick et al. Clinical Science. 2001; 100:395-40.*

Electromodulated Release of Nitric Oxide Through Polymer Material from Reservoir of Inorganic Nitrite Salt. Hofler et al. RSC Adv. Jan. 1, 2012; 2(17): 6765-6767.*

Electrochemically Modulated Nitric Oxide Release From Flexible Silicone Rubber Patch: Antimicrobial Activity for Potential Wound Healing Applications. Lee et al. ACS Biomater. Sc. Eng. 2016; 2, 1432-1435.*

Catalytic generation of nitric oxide from nitrite at the interface of polymeric films doped with lipophilic Cu(II)-complex: a potential route to the preparation of thromboresistant coatings. Oh et al. Biomaterials. 2004; 25, 283-293.*

Lee, Wh et al., "Electrochemically Modulated Nitric Oxide Release From Flexible Silicone Rubber Patch: Antimicrobial Activity for Potentrial Wound Healing Applications"; ACS Biomaterials Science & Engineering, vol. 2, No. 9, pp. 1432-1435; Aug. 2, 2016; Abstract; p. 1433.

Sanchez-Cruz, et al., "Quinone-Enhanced Reduction of Nitric Oxide by Xanthine/Xanthine Oxidase"; Chemical Research in Toxicology, vol. 22, No. 5; Mar. 20, 2009; Abstract; pp. 1, 3, 13.

Snijder, et al., "Exogenous administration of thiosulfate, a donor of hydrogen sulfide, attenuates angiotensin II-induced hypertensive heart disease in rats"; British Journal of Pharmacology, vol. 172, No. 6, pp. 1494-1504; Mar. 1, 2015; Title; Abstract; p. 1500.

My, et al., "Regulation of vascular nitric oxide in vitro and in vivo; a new role for endogenous hydrogen sulphide?"; British Journal of Pharmacology, vol. 149, pp. 625-634; Oct. 3, 2006; Abstract.

* cited by examiner

ELECTROCHEMICAL GASOTRANSMITTER GENERATING COMPOSITIONS AND METHODS OF USING SAME AND DRESSINGS AND TREATMENT SYSTEMS INCORPORATING SAME

RELATED APPLICATION DATA

This application claims the priority benefit of U.S. Provisional Application Ser. No. 62/457,039, filed Feb. 9, 2017, which is hereby incorporated in its entirety herein by reference.

FIELD OF THE INVENTION

The present invention relates to compositions that include one or more electrochemical mediators to generate one or more gasotransmitters, especially nitric oxide and hydrogen sulfide, as well as to therapeutic methods applying same, and to dressing articles and systems for the application thereof to target tissue sites.

BACKGROUND OF THE INVENTION

In the last two decades the importance of gasotransmitters in biological processes has been recognized, especially that of nitric oxide (NO) and hydrogen sulfide which have been implicated in a number of bioregulatory processes including normal physiological control of blood pressure, macrophage destruction of foreign pathogens, ischemic reperfusion injury, hemorrhagic shock, platelet aggregation, and neurotransmission. Recent research has further demonstrated that they possess a broad-spectrum of antimicrobial and anti-viral activity and may be used as an alternative to conventional antibiotics for drug resistant bacteria. In addition, gasotransmitters may also be used to alleviate inflammation and promote wound healing.

However, as gases at ambient temperature and atmospheric pressure, with short half-lives in physiological milieu it has proved relatively challenging to deliver gasotransmitters in a controlled and targeted manner. The use of gasotransmitters is further complicated by the time dependent concentration profile that is common in biological systems such as wound healing. In order to utilize gasotransmitters and mimic their bioregulatory function, they must be delivered in a manner that allows the flux (concentration) to be varied in a time dependent manner.

The present disclosure relates generally to gasotransmitter delivery formulations and devices. In the invention disclosed herein, the amount of gasotransmitter that is generated may be controlled in order to have a desired effect in a particular application. As one example, periodic gasotransmitter generation may be used for dispersing biofilm and killing bacteria. As another example, a steady physiologically-relevant flux of gasotransmitter for a predetermined time period may be generated to reduce thrombus formation and prevent infection. As still another example, a variable flux of gasotransmitter can be generated to deliver a physiologically-relevant time dependent concentration profile of gasotransmitter, to assist in wound healing for example.

In the last two decades the importance of gasotransmitters in biological processes has been recognized. It has become apparent that these gaseous signaling molecules are crucially important in a wide range of biological processess[1,2,3]. Endogenous gasotransmitters with their profound effects on mammalian physiology have, potentially, major implications in therapeutic applications[4]. The potential of gasotransmitters has been investigated for the nitric oxide[5,6,7] and hydrogen sulfide[8-10] treatment of neuropathy, tissue[11,12], platelet[13] and blood preservation[14], reperfusion injury[13-18], wound healing[21-25] and control of bacterial infections[26-29]. These studies have clearly demonstrated the therapeutic value of gasotransmitters.

To apply gasotransmitters in a clinical setting requires delivery to the situs of action. US20070065473A1 and PCT/US2012/058564 describe the delivery of gaseous nitric oxide as a cosmetic and wound healing agent. This approach has the clear disadvantage that delivery requires sealing the area to be treated. To overcome this issue, the generation of nitric oxide at the situs of action has been attempted. US20110104240A1 describes a method of generating nitric oxide by reduction of nitrite with an enzyme or living cell within a wound dressing. US20150297782 A1 describes the generation of nitric oxide in situ by the reaction of citric acid and nitrite ions within a dressing or article contacting a wound. Another attempt to deliver nitric oxide in a controlled and targeted manner is through acid decomposition of nitrite salts as described by Edixomed in WO/2014/188175A. These approaches deliver nitric oxide from a solid formulation but with limited control over the release profile.

U.S. Pat. No. 6,737,447 B1 uses an alternative approach to the generation of nitric oxide at the site of action. Nitric oxide is delivered bound to a polymer that forms part of the dressing. Release is triggered by exudate from the wound. WO2000030658 A1 describes the delivery of nitric oxide from the natural polymer chitosan. Another approach is described by BASF in US application U.S. Ser. No. 13/975, 930 and Novan Inc. US 20140134321 and US 20140171395. While these polymers allow nitric oxide to be delivered as a solid, there is limited control over the release profile.

A further attempt to deliver nitric oxide in a controlled and targeted manner is through electrochemical reduction of nitrite to nitric oxide as described in U.S. Pat. No. 9,480,785. The electrochemical generation of nitric oxide is achieved by generation of copper (I) at an electrode. This approach, like the invention described herein, utilizes electrochemical reduction of nitrite to nitric oxide. In contrast to U.S. Pat. No. 9,480,785 the present invention uses an organic mediator and thus avoids issues with electrode passivation and compatibility with open wounds.

The application of nitric oxide has been relatively limited because of the absence of a controlled and targeted delivery method or material. Therefore, there is a need for a gasotransmitter delivery system, that can deliver these species in a temporally, spatially and targeted manner. Gasotransmitters are endogenously generated molecules of gas.

SUMMARY OF THE INVENTION

The present invention relates to compositions comprising an organic electrochemical mediator, and a gasotransmitter generating salt which upon reduction, such as through action of an electrolytic cell, generates a gasotransmitter especially nitric oxide or hydrogen sulfide.

Gasotransmitters are among gaseous signaling molecules whether synthesized internally (endogenously) in the organism, tissue or cell or are received by the organism, tissue or cell from the outside; and that transmit chemical signals that induce certain physiological or biochemical changes in the organism, tissue or cell. The term is applied to, for example, oxygen, carbon dioxide, nitric oxide, carbon monoxide, hydrogen sulfide, sulfur dioxide, nitrous oxide, hydrogen cyanide, ammonia, methane, hydrogen, ethylene, etc.

The present invention also relates to compositions comprising an organic electrochemical mediator, and a soluble nitrite or nitrate salt.

The present invention also relates to compositions comprising an organic electrochemical mediator and a sulfite, thiosulfate, thiosulfite or sulfate salt.

The present invention also relates to methods for providing one or more health benefits to a subject by exposing a targeted tissue site to reaction product of the gasotransmitter generating compositions, typically by bringing about a gasotransmitter generating electrolytic reaction within therapeutic proximity to the targeted tissue site. As used herein, the term "tissue site" includes, without limitation, a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead tissue areas in which it is desired to bring about the effect of a gasotransmitter, such as to add or promote the growth of additional tissue. For example, reduced pressure tissue treatment may be used in certain tissue areas to grow additional tissue that may be harvested and transplanted to another tissue location. The tissue may be that of any mammal, such as a mouse, rat, rabbit, cat, dog, pig, or primate, including humans that are being treated as patients. Also, the wound at the tissue site may be due to a variety of causes, including trauma, surgery, degeneration, and other disease states.

The present invention also relates to the generation of gasotransmitters at the site of action by applying a voltage to the gasotransmitter generating compositions. For instance, the present invention includes a method of treating a variety of trauma and disease states by applying a therapeutically effective amount of at least one gasotransmitter thereto; i.e., by bringing a composition according to the present invention into therapeutic proximity (meaning within sufficient proximity to be able to effectively dose the gasotransmitter generated from electrolytic reaction involving the gasotransmitter-generating compositions) with a disease-affected or traumatized tissue, exposing the composition to a voltage.

In some embodiments, the amount and rate of the release of gasotransmitter is regulated by adjusting the formulation and/or the current.

The present invention also includes therapeutic systems for bringing one or more gastransmitters into therapeutic contact or influence at a tissue site. Such systems include dressings, bandages and the like adapted to generate and apply one or more gastransmitters at a tissue site, with optional active control of gasotransmitter generation.

The present invention further includes therapeutic dressings, and bandages containing same, comprising: (a) a gasotransmitter-generating composition; (b) a carrier adapted to contain the gasotransmitter-generating composition; and (c) a source of current in electrical contact with the gasotransmitter-generating composition, with an optional preferred voltage controller controlling the current from the source of current. The bandage of the present invention generally comprises (a) a dressing generally comprising: (i) an organic electrochemical mediator; and (ii) a gasotransmitter salt which converts into a gasotransmitter; (b) an anode and cathode in electrical contact with the dressing so as to apply a current thereto, whereby to convert the gasotransmitter salt into a gasotransmitter; (c) an electric power source in electrical contact with the anode and cathode (such as a battery); and (d) voltage controller controlling the current from the electric power source.

The present invention further includes a bandage system comprising: (a) a bandage comprising a dressing comprising: (i) an organic electrochemical mediator; and (ii) a gasotransmitter salt which converts into a gasotransmitter; (b) an anode and cathode in electrical contact with the dressing so as to apply a current thereto, whereby to convert the gasotransmitter salt into a gasotransmitter; and (c) an electric power source in electrical contact with the anode and cathode and external to the bandage; and (d) voltage controller controlling the current from the electric power source.

The dressings and bandage optionally may include a microprocessor having programming instructions adapted to control the voltage controller so as to be able to vary the amount of current and/or the time duration of application of the current from said electric power source.

Objects of the present invention will be appreciated by those of ordinary skill in the art from reading the detailed description of the preferred embodiments which follow, such description being merely illustrative of the present invention.

DETAILED DESCRIPTION OF THE INVENTION

Figure 1:
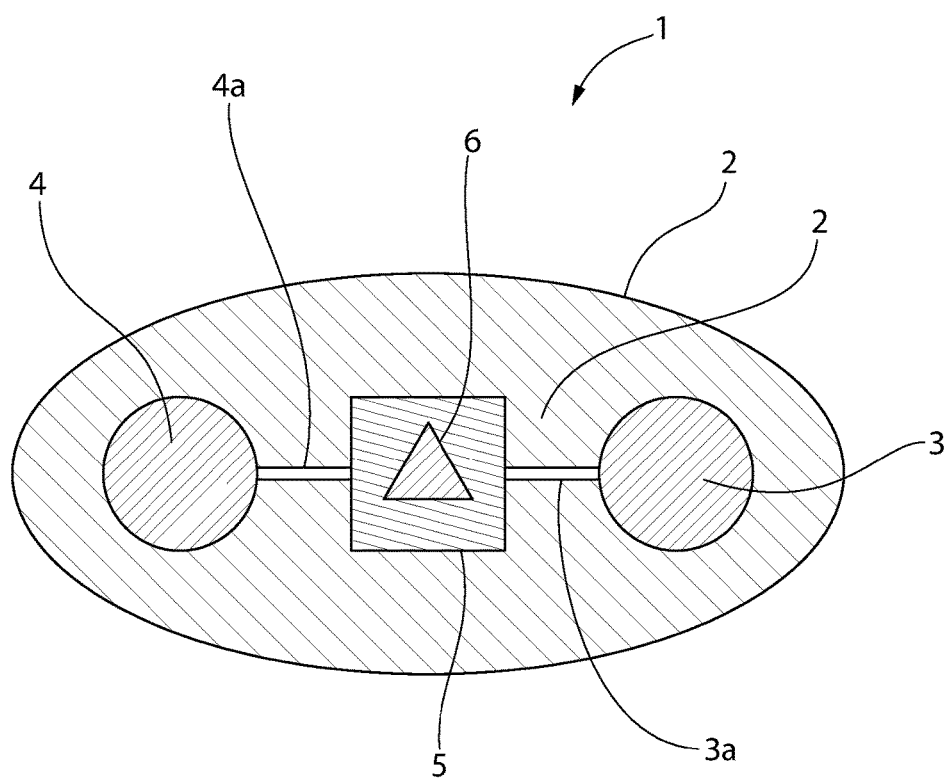
FIG. 1 shows a plan view schematic of a wound dressing integrating a gasotransmitter composition of matter of the present invention, as well as embodying a gasotransmitter release system of one embodiment of the present invention.

The foregoing and other aspects of the present invention will now be described in more detail with respect to the description and methodologies provided herein. It should be appreciated that the invention may be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. The term gasotransmitter salt refers to salts that when used in the present invention generate gasotransmitters. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

The present invention relates to electrochemically mediated compositions compromising an electrochemical mediator and a nitrite, nitrate, sulfite, thiosulfate, thiosulfite or sulfate salt. Still further, the present invention also relates to methods for providing one or more health benefits to a subject by exposing a targeted site to the gasotransmitter generating composition. In some embodiments, the amount and rate of the release of gasotransmitters may be regulated by adjusting the formulation and/or the applied current.

Electrochemical Mediator

The electrochemical mediator comprises: (1) an organic redox moiety and (2) a solubilizing moiety. In one embodiment the redox moiety is an organic moiety that is reduced at an electrode at a potential of from about −0.1 V to about −2.0 V preferably from about −0.5 V to about −1.7 V, preferably from about −0.75 V to about −1.5 V. Upon reduction the redox mediator forms a single electron reduced species that diffuses in the aqueous solution and reduces the gasotransmitter generating salt via electron transfer. In order to reduce the gasotransmitter generating salt the mediator should have a reduction potential, in its reduced state, greater than that required for the reduction of the salt to the gasotransmitter (e.g., such as the reduction of nitrate salt to nitric oxide).

The redox moiety of the electrochemical mediator of the present invention may be any moiety functionally adapted to perform the described redox mediation function, such as those selected from the group consisting of ketones, benzophenones, quinones, fluoresceins, xanthones, and thioxanthones, and derivatives thereof.

In one embodiment the electrochemical mediator of the present invention may be soluble in water.

If aqueous solubility is desired the electrochemical mediators of the present invention may incorporate polar functional groups, such as the alcohol, amine, amide, carboxylic acid, sulfonic acid and phosphate groups, which either ionize or are capable of relatively strong intermolecular forces of attraction with water (hydrogen bonding), will usually result in analogues with an increased water solubility. Acidic and basic groups are particularly useful. For purposes of the present invention, the term "water solubilizing moiety" refers to a moiety that is attracted to water and dissolves in water to form a homogenous solution. In one embodiment the water solubilizing moiety is selected from the group consisting of alcohol, amine, amide, carboxylic acid, sulfonic acid and phosphate groups. In another embodiment, the hydrophilic moiety is selected from the group consisting of water soluble oligomers, water soluble polymers and water soluble copolymers. In one preferred embodiment, the hydrophilic moiety may be selected from carboxylic acid and sulfonic acid. In another preferred embodiment the hydrophilic group is selected from the group consisting of alkylene oxide oligomers, alkylene oxide polymers, alkylene oxide copolymers, ethylene glycol, vinyl alcohol, vinyl pyrrolidone, acrylic acid, methacrylic acid, acrylamide, cellulose, carboxymethyl cellulose, chitosan, dextran, 2-ethyl-2-oxazoline, hydroxyethyl methacrylate, vinyl pyridine-N-oxide, diallyl dimethyl ammonium chloride, maleic acid, lysine, arginine, histidine, aspartic acid, glutamic acid, serine, threonine, asparagine, glutamine, isopropyl acrylamide, styrene sulfonic acid, vinyl methyl ether, vinyl phosphoinic acid, ethylene imine, and mixtures thereof. In one especially preferred embodiment, the hydrophilic moiety may be selected from the group consisting of alkylene oxide oligomer polymers, alkylene oxide oligomer copolymers, vinyl alcohol, vinyl pyrrolidone, acrylic acid, acrylamide, cellulose, and mixtures thereof.

For purposes of the present invention, the term "redox moiety" refers to an organic moiety that is capable of being reduced at an electrode to form a radical anion that in turn will reduce the gasotransmitter salt.

Electrochemical Composition

The present invention relates to an electrochemical composition that includes the electrochemical mediator, as described in further detail above, and a gasotransmitter salt.

The electrochemical composition may be an aqueous solution, emulsion, solid, gel, hydrogel, organogel, or incorporated into a material, such as a film. In another embodiment, the individual components of the electrochemical composition may be incorporated into both an composition and a material, such as a film. In one embodiment, the electrochemical mediator may be included in a film and the electron donor and/or nitrite may be included in a composition. It will be understood that in this particular embodiment, a film comprising an electrochemical mediator may be applied to a surface and a composition comprising a gasotransmitter salt may be applied separately.

However, if the electrochemical mediator is in aqueous composition, the composition may comprise from 0.1% to 99%, by weight of the composition, of water. It will therefore be understood that the electrochemical mediator can be in concentrated or diluted form. It is further contemplated that all or a portion of the water may be replaced with another solvent such as ethanol, glycol, glycol-ethers, glycerin, water soluble acetates ethers and alcohols.

As noted above, the present invention relates to electrochemical compositions that include the electrochemical mediator and a gasotransmitter salt. In such embodiments it will be understood that the electrochemical mediator is reduced at an electrode then reacts with gasotransmitter salt in the reduced form to generate the gasotransmitters. It will also be understood that the gasotransmitter salt can be converted into a gasotransmitter upon triggering by the electrochemical mediator after electron transfer at the electrode. It will be understood that the electrochemical mediator is substantially unreactive with the nitrite salt without activation by the electrode.

In the present embodiment, electron transfer to the electrochemical mediator at the electrode allows the reaction to progress to create gasotransmitters. In some embodiments the gasotransmitter may act to control blood pressure, macrophage destruction of foreign pathogens, and neurotransmission, provide a broad-spectrum of antimicrobial activity and alleviate inflammation and promote wound healing Gasotransmitter Salt The electrochemical composition of the present invention comprises a gasotransmitter salt. When used in the electrochemical composition of the present invention, the gasotransmitter salt is converted into a gasotransmitter by reduction.

In one aspect of the present invention, the gasotransmitter salt is a nitrite or nitrate salt with the formula:

$$A[NO_x]_m$$

wherein x is 2 or 3 and A is selected from the group consisting of monovalent cations, divalent cations, and trivalent cations; preferably A is selected from the group consisting of Aluminum, Barium, Calcium, Cobalt, Chromium, Copper, Iron, Lithium, Potassium, Rubidium, Magnesium, Manganese, Molybdenum, Nickel, Sodium, Titanium, Vanadium, Zinc, ammonium, alkyl-ammonium, aryl-ammonium, and mixtures thereof; more preferably A is selected from the group consisting of lithium, sodium, potassium, magnesium, calcium, ammonium, and mixtures thereof.

In another aspect the gasotransmitter salt is a sulfate, sulfite, or thiosulfate salt with the formula:

$$A[S_aO_b]_y$$

wherein A is selected from the group consisting of monovalent cations, divalent cations, and trivalent cations; preferably A is selected from the group consisting of Aluminum, Barium, Calcium, Cobalt, Chromium, Copper, Iron, Lithium, Potassium, Rubidium, Magnesium, Manganese, Molybdenum, Nickel, Sodium, Titanium, Vanadium, Zinc, ammonium, alkyl-ammonium, aryl-ammonium, and mixtures thereof; more preferably A is selected from the group consisting of lithium, sodium, potassium, magnesium, calcium, ammonium, and mixtures thereof. The coefficient a may be 1 or 2, and coefficient b may be 3 or 4.

Devices and Systems

In order to generate gasotransmitters from the compositions described herein, a voltage must be applied to the composition. The voltage applied must be greater than the reduction potential of the electrochemical mediator in the gasotransmitter generating composition. Though the form of the device may be tailored to the desired application, the device must contain the following elements:

1. Electrodes that contact the composition and transfer electrons to and from said composition. The electrode may be selected from any convenient electrode material known to those skilled in the art including but not limited to copper, aluminum, conductive carbon. Preferably the electrode is flexible. Preferably the electrode is a flexible carbon electrode.

2. A power source capable of generating the potential required for the reduction or oxidation of the electrochemical mediator. The voltage may be supplied by any convenient power source known to those skilled in the art, including but not limited to potentiostats, batteries, and supercapacitors. Preferably the power source is flexible. Preferably the power source is a flexible battery or supercapacitor.

3. A non-conductive substrate of a carrier material, including but not limited to polyethylene, polypropylene and polyester films and non-wovens, cellulose substrates such as cotton, chitosan, and collagen.

4. Electrical connection between the power source and the electrodes.

The devices and systems of the present invention may be in the form of therapeutic dressings, or bandages comprising same, comprising: (a) a gasotransmitter-generating composition; (b) a carrier adapted to contain the gasotransmitter-generating composition; (c) an anode and cathode in electrical contact with the dressing so as to apply a current thereto, whereby to convert the gasotransmitter salt into a gasotransmitter; and (d) a source of current in electrical contact with the gasotransmitter-generating composition, with an optional preferred voltage controller controlling the current from the source of current, as described herein.

The devices and systems may include a microprocessor to exert control over the amount, timing and duration of current application to the electrolytic cell.

Optional Additives

The electrochemical compositions of the invention may also contain additional adjunct additives. The precise nature of these additional components and levels of incorporation thereof will depend on the physical form of the composition, and the precise nature of the cleaning, disinfecting or health benefit for which it is to be used. It will be understood that some of the adjunct additives noted below will have electrochemical properties, but it will be further understood that such additives will not replace the components noted above.

Topical Compositions

According to some embodiments of the present invention, provided herein are topical compositions. In some embodiments a topical composition of the present invention is in the form of a hydrogel. "Hydrogel," as used herein, refers to a hydrophilic gel comprising a gel matrix and water. In some embodiments, a topical composition of the present invention comprises at least one polyhydric alcohol, at least one viscosity increasing agent, and water.

Exemplary polyhydric alcohols that may be present in a composition of the present invention include, but are not limited to, glycerol, propylene glycol, polyethylene glycol, polypropylene glycol, triethylene glycol, neopental glycols, triethanolamine, diethanolamine, ethanolamine, butylene glycol, polyethylene glycol, n-methyl diethanolamine, isopropanolamine, sorbitol, arabitol, erythritol, HSH, isomalt, lactitol maltitol, mannitol, xylitol, threitol, ribitol, galactitol, fucitol, iditol, inositol, volemitol, and any combination thereof. In some embodiments, a composition of the present invention comprises glycerol.

A polyhydric alcohol may be present in a composition of the present invention in an amount of about 1% to about 30% by weight of the composition or any range and/or individual value therein, such as, but not limited to, about 1% to about 20% or about 5% to about 15% by weight of the composition. In certain embodiments, a polyhydric alcohol is present in a composition of the present invention in an amount of about 1%, 2%, 3%, 4%, 5%, 6%, 7%, 8%, 9%, 10%, 11%, 12%, 13%, 14%, 15%, 16%, 17%, 18%, 19%, or 20% by weight of the composition or any range and/or individual value therein.

Exemplary viscosity increasing agents that may be present in a composition of the present invention include, but are not limited to, a carboxypolymethylene; a polyacrylic polymer such as polyacrylic acid, a polyacrylate polymer, a cross-linked polyacrylate polymer, a cross-linked polyacrylic acid, and mixtures thereof; a cellulose ether such as hydroxyalkyl cellulose polymers such as hydroxypropyl methyl cellulose (HPMC), hydroxypropyl cellulose, hyrdoxyethyl cellulose, methyl cellulose, carboxymethyl cellulose, and mixtures thereof; a methacrylate; a polyvinylpyrrolidone; cross-linked polyvinyl pyrrolidone; polyvinylpyrrolidone-vinyl acetate copolymer; polyvinylalcohol; polyethylene oxide; polyethylene glycol; polyvinylalkyl ether-maleic acid copolymer; a carboxy vinyl polymer; a polysaccharide; a gum such as sodium alginate, carrageenan, xantham gum, gum acacia, arabic gum, guar gum, pullulan, agar, chitin, chitosan, pectin, karaya gum, zein, hordein, gliadin, locust bean gum, tragacantha, and mixtures thereof; a protein such as collagen, whey protein isolate, casein, milk protein, soy protein, gelatin, and mixtures thereof; a starch such as maltodextrin, amylose, high amylose starch, corn starch, potato starch, rice starch, tapioca starch, pea starch, sweet potato starch, barley starch, wheat starch, waxy corn starch, modified starch (e.g. hydroxypropylated high amylose starch), dextrin, levan, elsinan, gluten, and mixtures thereof; bentonite; calcium stearate; ceratonia; colloidal silicon dioxide; dextrin; hypromellose; polycarbophil; kaolin; saponite; sorbitan esters; sucrose; sesame oil; tragacanth; potassium alginate; povidone; sodium starch glycolate; phospholipids; and any combination thereof.

In some embodiments, a composition of the present invention comprises a carboxypolymethylene, such as, but not limited to, those commercially available from Lubrizol Corporation of Wickliffe, Ohio under the trade name Carbopol®. Exemplary Carbopol® polymers that may be present in a composition of the present invention include, but are not limited to, Carbopol® 974P NF polymer, such as Type A, Type B and/or Type C Homopolymers; Carbopol® Ultrez 10, 20, 21 NF polymer; Carbopol® 971P NF polymer; Carpobol® 980P polymer, Carbopol® ETD 2020 NF polymer, Carbopol® 71 G NF polymer, Carbopol® 981P NF polymer, Carbopol® 970P NF polymer, Carbopol® 981 P NF polymer, Carbopol® 5984P NF polymer, Carbopol® 934P NF polymer, Carbopol® 940P NF polymer, Carbopol® 941P NF polymer, Carbopol® 13242 NF polymer, Carbopol® AA-1 USP NF polymer, Carbopol® TR1 NF polymer, Carbopol® TR2 NF polymer, Lubrizol Aqua CC polymer and SF-2 polymer, and any combination thereof.

A viscosity increasing agent may be present in a composition of the present invention. In some embodiments, a composition of the present invention comprises at least two viscosity increasing agents that may be the same or different. In some embodiments, a first viscosity increasing agent may be present in a composition of the present invention in an amount of about 0.01% to about 5% by weight of the composition or any range and/or individual value therein, such as, but not limited to, about 0.05% to about 3% or about 0.1% to about 1.5% by weight of the composition. In certain embodiments, a first viscosity increasing agent is present in a composition of the present invention in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, or 5% by weight of the composition or any range and/or individual value therein.

Water may be present in a composition of the present invention in an amount of about 0.1% to about 99% by weight of the composition or any range and/or individual value therein, such as, but not limited to, about 75% to about 95% or about 80% to about 90% by weight of the composition. In certain embodiments, water is present in a composition of the present invention in an amount of about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the composition or any range and/or individual value therein.

In some embodiments, a composition of the present invention comprises at least one polyhydric alcohol present in an amount of about 1% to about 30% by weight of the composition, at least one viscosity increasing agent present in an amount of about 0.1% to about 5% by weight of the composition, and water present in an amount of about 70% to about 99% by weight of the composition. The composition may be in the form of a hydrogel. In certain embodiments, the viscosity increasing agent may be a carboxypolymethylene.

A composition of the present invention may comprise a preservative. A preservative may be present in a composition of the present invention in an amount of about 0.01% to about 1% by weight of the composition or any range and/or individual value therein, such as, but not limited to, about 0.05% to about 1% or about 0.1% to about 1% by weight of the composition. In certain embodiments, a preservative is present in a composition of the present invention in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% by weight of the composition or any range and/or individual value therein. Exemplary preservatives that may be present in a composition of the present invention include, but are not limited to, sorbic acid, benzoic acid, methyl-paraben, propyl-paraben, methylchloroisothiazolinone, metholisothiazolinone, diazolidinyl urea, chlorobutanol, triclosan, benzethonium chloride, p-hydroxybenzoate, chlorhexidine, digluconate, hexadecyltrimethyl ammonium bromide, alcohols, benzalkonium chloride, boric acid, bronopol, butylparaben, butylene calcium acetate, calcium chloride, calcium lactate, carbon dioxide, cationic, and bentonite, cetrimide, cetylpyridinium chloride, chlorhexidine, chlorobutanol, chlorocresol, chloroxylenol, citric acid monohydrate, cresol, dimethyl ether, ethylparaben, glycerin, hexetidine, imidurea, isopropyl alcohol, lactic acid, monothioglycerol, pentetic acid, phenol, phenoxyethanol, phenylethyl alcohol, phenylmercuric acetate, phenylmercuric borate, phenylmercuric nitrate, potassium benzoate, potassium metabisulfite, potassium sorbate, propionic acid, propyl gallate, propylene glycol, sodium acetate, sodium benzoate, sodium borate, sodium lactate, sodium sulfite, sodium propionate, sodium metabisulfite, xylitol, sulphur dioxide, carbon dioxide, and any combination thereof.

A composition of the present invention may comprise a neutralizing agent. A neutralizing agent may be present in a composition of the present invention in an amount sufficient to provide the composition with a pH of about 3 to about 8, or any range and/or individual value therein, such as, but not limited to, about 4 to about 7 or about 6 to about 7. In some embodiments, a neutralizing agent adjusts the pH of the composition. In certain embodiments of the present invention, a neutralizing agent is present in a composition of the present invention in an amount sufficient for the composition to have a pH of about 3, 3.5, 4, 4.5, 5, 5.5, 6, 6.5, 7, 7.5, or 8 or any range and/or individual value therein. Exemplary neutralizing agents that may be present in a composition of the present invention include, but are not limited to, bases such as sodium hydroxide, potassium hydroxide, and mixtures thereof; acids such as hydrochloric acid, citric acid, acetic acid, and mixtures thereof; sodium carbonate; trolamine; tromethamine; aminomethyl propanol; triisopropanolamine; aminomethyl propanol; tetrahydroxypropyl ethylenediamine; tetrasodium EDTA; suttocide A; and any combination thereof.

A composition of the present invention may be unbuffered or buffered. In some embodiments, a composition of the present invention may be unbuffered. In other embodiments, a composition of the present invention may be buffered. Exemplary buffers that may be present in composition of the present invention include, but are not limited to, acetic acid/acetate buffers; hydrochloric acid/citrate buffers; citrophosphate buffers; phosphate buffers; citric acid/citrate buffers; lactic acid buffers; tartaric acid buffers; malic acid buffers; glycine/HCl buffers; saline buffers such as phosphate buffered saline (PBS), Tris-buffered saline (TBS), Tris-HCl, NaCl, Tween buffered saline (TNT), phosphate buffered saline, Triton X-100 (PBT) and mixtures thereof; cacodylate buffers; barbital buffers; tris buffers; and any combination thereof.

In certain embodiments, a composition of the present invention may comprise a buffering agent. Exemplary buffering agents include, but are not limited to, citric acid, acetic acid, lactic acid, boric acid, succinic acid, malic acid, and any combination thereof. A buffering agent may be present in a composition of the present invention in an amount of about 0.01% to about 2% by weight of the composition or any range and/or individual value therein, such as, but not limited to, about 0.05% to about 1%, about 0.1% to about 0.5%, or about 0.1% to about 2% by weight of the composition. In certain embodiments, a buffering agent is present in a composition of the present invention in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% by weight of the composition or any range and/or individual value therein.

In some embodiments, a buffer is present in a composition of the present invention in an amount sufficient for the composition to have a pH of about 3 to about 8, or any range and/or individual value therein, such as, but not limited to, about 4 to about 7 or about 6 to about 7. In certain embodiments of the present invention, a buffer is present in a composition of the present invention in an amount sufficient for the composition to have a pH of about 3, 3.5, 4, 4.5, 5, 5.5, 6, 6.5, 7, 7.5, or 8 or any range and/or individual value therein.

A composition of the present invention may be antimicrobial. In some embodiments, a composition of the present invention comprises a preservative that is present in an amount sufficient to provide antimicrobial activity to the composition. In certain embodiments, a composition of the present invention comprises at least one polyhydric alcohol present in an amount of about 1% to about 30% by weight of the composition, at least one viscosity increasing agent present in an amount of about 0.1% to about 5% by weight of the composition, water present in an amount of about 70% to about 99% by weight of the composition, and at least one preservative in an amount of about 0.01% to about 1% by weight of the composition. The composition may be buffered to have a pH in a range of about 3 to about 8 or about 6 to about 8.

A composition of the present invention may have a viscosity in a range of about 5,000 cP to about 25,000 cP or any range and/or individual value therein, such as, but not limited to, about 5,000 cP to about 20,000 cP or about 7,000 cP to about 15,000 cP. In certain embodiments, a composition of the present invention may have a viscosity of about 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 24,500, or 25,000 cP or any range and/or individual value therein.

A composition of the present invention may comprise an active pharmaceutical ingredient (API). Any suitable API or combinations of APIs may be included in a composition of the present invention. Examples of APIs include, but are not limited to, antimicrobial agents, anti-acne agents, anti-inflammatory agents, analgesic agents, anesthetic agents, antihistamine agents, antiseptic agents, immunosuppressants, antihemorrhagic agents, vasodilators, wound healing agents, anti-biofilm agents, and any combination thereof. Exemplary APIs include, but are not limited to, those described in International Application Publication No. WO 2013/006608, which is incorporated herein by reference in its entirety. Alternatively, a composition of the present invention may not comprise an API.

Pharmaceutical Compositions

The present invention provides pharmaceutical compositions that may be administered topically. A pharmaceutical composition of the present invention may comprise, consist essentially of, or consist of a hydrophobic base and an amphiphilic compound. In particular embodiments of the present invention, a pharmaceutical composition further comprises a moisture activated active pharmaceutical ingredient. A pharmaceutical composition of the present invention may comprise an ointment, salve, cream, and/or the like.

"Hydrophobic base" as used herein refers to a natural and/or synthetic fat, wax, oil, and/or the like. Any suitable hydrophobic base may be used in a pharmaceutical composition of the present invention. In certain embodiments of the present invention, a pharmaceutical composition comprises two or more hydrophobic bases, such as, but not limited to, 2, 3, 4, 5, or more hydrophobic bases. Exemplary hydrophobic bases include, but are not limited to, branched and unbranched hydrocarbons, branched and unbranched hydrocarbon waxes, vaseline, hydrocarbon gel, liquid paraffin, white petrolatum, petrolatum, microcrystalline wax, andelilla wax, carnauba wax, lanolin (wool wax), wool wax alcohol, esparto grass wax, cork wax, guaruma wax, rice bran wax, sugar cane wax, berry wax, ouricury wax, soy wax, jojoba oil, uropygial grease, ceresine, paraffin waxes, micro waxes, plant oils, animal oils, carnauba wax, beeswax, cacao butter, hard fat, mineral oil, vegetable oil, avocado oil, borage oil, canola oil, castor oil, chamomile oil, coconut oil, corn oil, cottonseed oil, rapeseed oil, evening primrose oil, safflower oil, sunflower oil, soybean oil, sweet almond, palm oil, palm kernel oil, *arctium lappa* seed oil, sesame oil, *borgo officialis* seed oil, *brassica campestris oleifera* oil, *brevoortia* oil, *bubulum* oil, *cistus ladaniferus* oil, *elaeis guineensis* oil, almond oil, pine oil, olive oil, peanut oil, wheat germ oil, grape seed oil, thistle oil, lard, tallow, palm olein, illipe butter, shea butter, cocoa butter, kokum butter, sal butter, lecithin, japan wax lanolin, partially hydrogenated vegetable oils, hydrophobic polymers, and any combination thereof.

In some embodiments of the present invention, a hydrophobic base may comprise a hydrophobic polymer. Any suitable hydrophobic polymer may be used in a pharmaceutical composition of the present invention. Exemplary hydrophobic polymers include, but are not limited to hydrocarbon polymers and/or co-polymers, aromatic polyurethanes, silicone rubber, polysiloxanes, polycaprolactone, polycarbonate, polyvinylchloride, polyethylene, poly-L-lactide, poly-DL-glycolide, polyetheretherketone (PEEK), polyamide, polyimide and polyvinyl acetate. In particular embodiments of the present invention, a pharmaceutical composition of the present invention comprises one or more hydrocarbon polymers and/or co-polymers. In certain embodiments, a pharmaceutical composition of the present invention comprises one or more hydrocarbon polymers and/or co-polymers, such as, but not limited to, those commercially available from Calumet Specialty Products Partners of Indianapolis, Ind. under the trademark Versagel® and/or those commercially available from Croda International Plc of East Yorkshire, United Kingdom under the trade name Crodabase SQ.

In some embodiments of the present invention, a hydrophobic polymer may act as thickening and/or gelling agent in a pharmaceutical composition. Specifically, a hydrophobic polymer may act as a visco-elastic substance and may retain the composition at the site of application, along with any compounds dispersed therein (e.g., an active pharmaceutical ingredient, etc.). A hydrophobic polymer may be present in a pharmaceutical composition of the present invention at a concentration from about 30% to about 60% by weight or any range therein, such as, but not limited to, from about 35% to about 55% by weight or about 40% to about 50% by weight.

In particular embodiments of the present invention, a hydrophobic base comprises one or more plant and/or mineral oils. Any suitable oil may be used in the pharmaceutical compositions of the present invention. Exemplary mineral oils include, but are not limited to, light mineral oil, white mineral oil, paraffinic oils, napthenic oils, aromatic oils, and any combination thereof. An oil (e.g., plant and/or mineral oil) may be present in a pharmaceutical composition of the present invention at a concentration from about 1% to about 30% by weight or any range therein, such as, but not limited to, from about 5% to about 20% by weight or about 5% to about 15% by weight.

In some embodiments of the present invention, a hydrophobic base, such as, but not limited to, an oil (e.g., a plant and/or mineral oil), may be used to tune the viscosity and/or spreadability of the pharmaceutical composition. For example, a low viscosity hydrophobic base, such as light mineral, may be used to thin (i.e., reduce the viscosity) a pharmaceutical composition, such as, a pharmaceutical composition comprising a high viscosity hydrophobic base. This may enable the application of a pharmaceutical composition of the present invention over a wide area, and may serve to maintain any compounds dispersed therein (e.g., an active pharmaceutical ingredient, etc.) at the site of application. In certain embodiments of the present invention, a hydrophobic base comprises a mineral oil and a hydrophobic polymer.

A hydrophobic base may be present in a pharmaceutical composition of the present invention at a concentration from about 35% to about 90% by weight or any range therein, such as, but not limited to, from about 40% to about 80% by weight or about 50% to about 70% by weight. In certain embodiments of the present invention, a hydrophobic base is present in a pharmaceutical composition of the present invention at a concentration from about 45% to about 55% by weight.

"Amphiphilic compound" as used herein refers to a compound comprising hydrophilic and hydrophobic properties. An amphiphilic compound may comprise two or more compounds, each of which may provide the hydrophilic property and/or the hydrophobic property. In some embodiments, the amphiphilic compound comprises one compound having hydrophilic and hydrophobic properties. In particular embodiments of the present invention, an amphiphilic compound may absorb moisture without substantially absorbing vaporous moisture. The absorption of moisture may allow for activation of a moisture activated active pharmaceutical ingredient in a pharmaceutical composition of the present invention upon contact with the moisture, but not upon contact with vaporous moisture. "Substantially absorbing" (and grammatical variations thereof) as used herein means that the amount of vaporous moisture absorbed is more than 2% by weight of an amphiphilic compound. Thus, an amphiphilic compound of the present invention absorbs vaporous moisture by less than about 2%, 1.5%, 1%, 0.5%, 0.25% by weight of an amphiphilic compound or any range therein. In some embodiments of the present invention, an amphiphilic compound may prevent and/or minimize a pharmaceutical composition of the present invention from substantially absorbing vaporous moisture, thereby moisture may be present in a pharmaceutical composition of the present invention by less than about 2%.

"Moisture" as used herein refers to a liquid, such as, but not limited to, a bodily fluid such as, but not limited to, blood, sweat, mucus, saliva, sebum, tears, exudate, and/or vaginal secretions; water; deoxygenated water; saline solutions; acidic or alkaline buffer solutions; and/or any combination thereof. "Vaporous moisture" as used herein refers to moisture in the gas phase. For example, vaporous moisture, includes, but is not limited to, water vapor. Thus, in some embodiments of the present invention, an amphiphilic compound may prevent and/or minimize the absorption of water vapor, thereby, when the active pharmaceutical ingredient (API) comprises a moisture activated pharmaceutical ingredient, the API in a pharmaceutical composition of the present invention is not activated by the vaporous moisture (e.g., water vapor). In contrast, an amphiphilic compound may absorb and/or allow moisture (e.g., water, a bodily fluid, etc.) to be absorbed when a pharmaceutical composition of the present invention is contacted with the moisture, thereby activating the API when the API comprises a moisture activated active pharmaceutical ingredient.

In particular embodiments of the present invention, an amphiphilic compound absorbs water vapor by less than about 2% by weight or about 1% by weight. This may minimize and/or prevent a pharmaceutical composition of the present invention from absorbing water vapor and thus water may be present in a pharmaceutical composition of the present invention by less than about 2% by weight or about 1% by weight water. In certain embodiments of the present invention, an amphiphilic compound absorbs less than about 0.5% by weight water vapor and thus a pharmaceutical composition of the present invention may comprise less than about 0.5% by weight water.

An amphiphilic compound may have a hydrophilic-lipophilic balance (HLB) value of 12 to 20 or any range therein, such as, but not limited to, 15 to 20 or 18 to 20. In certain embodiments of the present invention, an amphiphilic compound comprises a HLB value of 19.

Exemplary amphiphilic compounds include, but are not limited to, fatty acid esters. One or more fatty acid ester(s) may be present in the pharmaceutical compositions of the present invention, such as 2, 3, 4, or more fatty acid esters. Exemplary fatty acid esters include, but are not limited to, C6-C22 alkyl and/or alkenyl fatty acid esters such as methyl laurate, ethyl laurate, ethyl myristate, ethyl palmitate, ethyl linoleate, propyl isobutylate, isopropyl laurate, isopropyl myristate, isopropyl palmitate, oleyl myristate, oleyl stearate, and oleyl oleate; ether-esters such as fatty acid esters of ethoxylated fatty alcohols; polyhydric alcohol esters such as ethylene glycol mono- and di-fatty acid esters, diethylene glycol mono- and di-fatty acid esters; polyethylene glycol (6-2000) fatty acid mono- and/or diesters such as PEG-6-laurate, PEG-6-stearate, PEG-8-dilaurate, PEG-8-distearate, etc.; polyethylene glycol glycerol fatty acid esters such as PEG-20-glyceryl laurate, PEG-20-glyceryl stearate, and PEG-20-glyceryl oleate; propylene glycol mono- and di-fatty acid esters; polypropylene glycol 2000 monooleate; polypropylene glycol 2000 monostearate; ethoxylated propylene glycol monostearate; glyceryl mono- and di-fatty acid esters; polyglycerol fatty acid esters such as polyglyceryl-10 laurate, etc.; ethoxylated glyceryl monostearate; 1,3-butylene glycol monostearate; 1,3-butylene glycol distearate; polyoxyethylene polyol fatty acid ester; sorbitan fatty acid esters including sorbitan trioleate and sorbitan monolaurate; polyethylene glycol sorbitan fatty acid esters such as PEG-6 sorbitan monooleate; polyoxyethylene sorbitan fatty acid esters including polyoxyethylene (20) sorbitan monolaurate; sucrose fatty acid esters such as saccharose monopalmitate and saccharose monostearate; wax esters such as beeswax, spermaceti, myristyl myristate, stearyl stearate and arachidyl behenate; polyethylene glycol alkyl ethers such as PEG-10 oleyl ether or PEG-9 cetyl ether; polyethylene glycol alkyl phenols such as PEG-10-100 nonyl phenol; polyoxyethylene-polyoxypropylene block copolymers such as poloxamer 188; sterol esters such as cholesterol fatty acid esters, and any combination thereof.

A fatty acid ester may comprise a polyethylene glycol (PEG) glyceride. The polyethylene glycol portion of a PEG glyceride may provide the hydrophilic property of an amphiphilic compound and may include, but is not limited to, PEG 5-1000 or any range therein, and any combination thereof. The glyceride portion of a PEG glyceride may provide the hydrophobic property of an amphiphilic compound and may include, but is not limited to, a natural and/or hydrogenated oil, such as but not limited to, castor oil, hydrogenated castor oil, vitamin A, vitamin D, vitamin E, vitamin K, a plant oil (e.g., corn oil, olive oil, peanut oil, palm kernel oil, apricot kernel oil, almond oil, etc.), and any combination thereof. Exemplary polyethylene glycol (PEG) glycerides include, but are not limited to, PEG-20 castor oil, PEG-20 hydrogenated castor oil, PEG-20 corn glycerides, PEG-20 almond glycerides; PEG-23 trioleate, PEG-40 palm kernel oil, PEG-8 caprylic/capric glycerides, PEG-6 caprylic/capric glycerides, lauroyl macrogol-32 glyceride, stearoyl macrogol glyceride, tocopheryl PEG-1000 succinate, and any combination thereof. In some embodiments of the present invention a fatty acid ester comprises a PEG 5-30 (i.e., PEG 5, 6, 7, 8, 9, 10, etc.) and a caprylic/capric glyceride. In particular embodiments of the present invention, a pharmaceutical composition comprises a PEG-5-caprylic/capric glyceride, a PEG-6-caprylic/capric glyceride, a PEG-7-caprylic/capric glyceride, and/or a PEG-8-caprylic/capric glyceride. In certain embodiments of the present invention, a pharmaceutical composition comprises one or more fatty acid esters such as, but not limited to, those commercially available from Sasol of Hamburg, Germany under the trademark SOFTIGEN®.

An amphiphilic compound may be present in a pharmaceutical composition of the present invention at a concentration from about 1% to about 30% by weight or any range therein, such as, but not limited to, from about 2% to about 20% by weight or about 5% to about 15% by weight. In certain embodiments of the present invention, an amphiphilic compound is present in a pharmaceutical composition of the present invention at a concentration of about 10% by weight.

A pharmaceutical composition of the present invention may further comprise one or more excipients. Excipients for use in pharmaceutical compositions are well-known in the art and examples may be found in the Handbook of Pharmaceutical Excipients (Rowe, R. C. et al., APhA Publications; 5th ed., 2005). Classes of excipients may include, but are not limited to, an emollient, a humectant, a cosolvent, a pH modifier, a water repelling agent, an anti-foaming agent, a surfactant, a solubilizer, a wetting agent, a penetration enhancer, an antioxidant, and/or a solvent. The excipients may be present in a pharmaceutical composition of the present invention at any suitable concentration.

In particular embodiments of the present invention, a pharmaceutical composition may further comprise a cosolvent. A cosolvent may be present in a pharmaceutical composition of the present invention at a concentration from about 1% to about 30% by weight or any range therein, such as, but not limited to, from about 2% to about 20% by weight or about 5% to about 15% by weight. In certain embodiments of the present invention, a cosolvent is present in a pharmaceutical composition of the present invention at a concentration from about 10% to about 15% by weight.

Exemplary cosolvents include, but are not limited to, a fatty acid ester, propylene glycol, glycerol, polyethylene glycol. In some embodiments of the present invention, a cosolvent may comprise a neutral oil. In certain embodiments of the present invention, a cosolvent comprises a caprylic and/or capric triglyceride such as, but not limited to, those commercially available from Sasol of Hamburg, Germany under the trademark MIGLYOL®.

The pharmaceutical compositions of the present invention may comprise a humectant. Any suitable humectant or combination of humectants may be used. A humectant may be present in a pharmaceutical composition of the present invention at a concentration from about 1% to about 25% by weight or any range therein, such as, but not limited to, from about 2% to about 20% by weight or about 5% to about 15% by weight. In certain embodiments of the present invention, a humectant is present in a pharmaceutical composition of the present invention at a concentration from about 10% to about 15% by weight.

Exemplary humectants include, but are not limited to, glycols, such as a polyhydric alcohol, diethylene glycol monoethyl ether and methoxypolyethyleneglycol; glycerols such as propylene glycol, glycerol, isopropanol, ethanol, ethylene glycol, polyethylene glycol, ethoxydiglycol or mixtures thereof; sugar polyols, such as sorbitol, xylitol and maltitol; polyols such as polydextroses; dimethyl isosorbide; quillaia; urea; and any combination thereof. In particular embodiments of the present invention, a humectant comprises an alkylene glycol, such as hexylene glycol, butylene glycol, pentylene glycol, and any combination thereof.

Oral Care Compositions

The electrochemical composition may be an oral care composition to be topically applied to the mucosal tissue of the oral cavity, to the gingival tissue of the oral cavity, to the surface of the teeth or any combination thereof. Examples of oral conditions such oral care actives address include, but are not limited to, appearance and structural changes to teeth, whitening, stain bleaching, stain removal, plaque removal, tartar removal, cavity prevention and treatment, inflamed and/or bleeding gums, mucosal wounds, lesions, ulcers, aphthous ulcers, cold sores and tooth abscesses, oral malodor, dental erosion, gingivitis, and/or periodontal disease. Oral conditions are further described in WO 02/02096A2.

The electrochemical composition may include one or more oral care additives. The oral care active can be any material that is generally recognized as safe for use in the oral cavity that provides changes to the overall health of the oral cavity, and specifically the condition of the oral surfaces the oral care active contacts. The electrochemical composition can comprise one or multiple oral care additives.

It is also contemplated that a single oral care product can comprise multiple electrochemical compositions, each of which comprises one or more oral care additives. Some oral care additives that are suitable for use in the electrochemical composition are discussed more fully below.

The electrochemical composition may include one or more gelling agents, which may also act as an adhesive agent to adhere the electrochemical composition to the plurality of teeth. The concentration of the gelling agent may be greater than about 2, 4, 6, 8, 10, 15, 20, 30, 40, 50, 60 or less than about 80, 70, 60, 50, 40, 30, or 20 percent by weight of the electrochemical composition.

Suitable gelling agents and/or adhesion agents useful in the present invention are described in U.S. Pat. Nos. 6,649,147; 6,780,401; 2004/0102554; 2005/0089819; 2003/0152528; U.S. Pat. No. 6,419,906; and 2005/0100515. Some of the gelling agents or adhesion agents may include silicone, polyethylene oxide, polyvinyl alcohol, poly alkyl vinyl ether-maleic acid copolymer (PVM/MA copolymer) such as, Gantrez AN 119, AN 139, and S-97, polyvinyl alcohol, polyacrylic acid, Poloxamer 407 (Pluronic), polyvinyl pyrrolidone-vinyl acetate copolymer (PVP/VA copolymer), such as Luviskol VA, and Plasdone S PVP/VA, polyvinyl pyrrolidone (PVP, e.g., K-15 to K-120), Polyquaterium-11 (Gafquat 755N), Polyquaterium-39 (Merquat plus 3330), carbomer or carboxypolymethylene (Carbopol), hydroxy propyl methyl cellulose, hydroxy ethyl cellulose, hydroxy propyl cellulose, carboxymethyl cellulose, gelatin and alginate salt such as sodium alginate, natural gums such as gum karaya, xanthan gum, Guar gum, gum arabic, gum tragacanth, and mixtures thereof.

A humectant or plasticizer may be included in the electrochemical composition, including glycerin, sorbitol, polyethylene glycol, propylene glycol, and other edible polyhydric alcohols. The humectants may be present between about 10% to about 95%, or between about 50% and about 80%, by weight of the electrochemical composition. An electrochemical composition can also include flavoring agents, sweetening agents, opacifiers, and coloring agents.

The electrochemical composition of the present invention may comprise a non-electrochemical anti-tartar agent. Anti-tartar actives known for use in dental care products include phosphates. Phosphates include pyrophosphates, polyphosphates, polyphosphates and mixtures thereof. Pyrophosphates are among the best known for use in dental care products. Pyrophosphate ions are delivered to the teeth and are derived from pyrophosphate salts. The pyrophosphate salts useful in the present compositions include the dialkali metal pyrophosphate salts, tetra-alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. While any of the above mentioned pyrophosphate salts may be used, tetrasodium pyrophosphate salt is preferred. In one embodiment the electrochemical composition comprises from about 0.5% to about 5% of a pyrophosphate by weight of the electrochemical composition. In another embodiment the electrochemical composition comprises from about 0.5% to about 3% of a pyrophosphate by weight of the electrochemical composition.

The pyrophosphate salts are described in more detail in Kirk & Othmer, Encyclopedia of Chemical Technology, Third Edition, Volume 17, Wiley-Interscience Publishers (1982), incorporated herein by reference in its entirety, including all references incorporated into Kirk & Othmer. Additional anticalculus actives include pyrophosphates or polyphosphates disclosed in U.S. Pat. No. 4,590,066 issued to Parran & Sakkab on May 20, 1986; polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict & Sunberg on Apr. 28, 1987; polyepoxysuccinates such as those disclosed in U.S. Pat. No. 4,846,650 issued to Benedict, Bush & Sunberg on Jul. 11, 1989; ethylenediaminetetraacetic acid as disclosed in British Patent No. 490,384 dated Feb. 15, 1937; nitrilotriacetic acid and related compounds as disclosed in U.S. Pat. No. 3,678,154 issued to Widder & Briner on Jul. 18, 1972; polyphosphonates as disclosed in U.S. Pat. No. 3,737,533 issued to Francis on Jun. 5, 1973, U.S. Pat. No. 3,988,443 issued to Ploger, Schmidt-Dunker & Gloxhuber on Oct. 26, 1976 and U.S. Pat. No. 4,877,603 issued to Degenhardt & Kozikowski on Oct. 31, 1989; all of these patents are incorporated herein by reference. Anticalculus phosphates include potassium and sodium pyrophosphates; sodium tripolyphosphate; diphosphonates, such as ethane-1-hydroxy-1,1-diphosphonate, 1-azacycloheptane-1,1-diphosphonate, and linear alkyl diphosphonates; linear carboxylic acids; and sodium zinc citrate.

Actives that may be used in place of or in combination with the pyrophosphate salt include such known materials as synthetic anionic polymers including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof. Other anti-tartar actives include sodium hexametaphosphate.

The electrochemical composition of the present invention may also comprise a non-electrochemical anti-caries agent. Fluoride ion sources are well known for use in oral care compositions as anticaries actives. Fluoride ions are contained in a number of oral care compositions for this purpose, particularly toothpastes. Patents disclosing such toothpastes include U.S. Pat. No. 3,538,230, Nov. 3, 1970 to Pader et al; U.S. Pat. No. 3,689,637, Sep. 5, 1972 to Pader; U.S. Pat. No. 3,711,604, Jan. 16, 1973 to Colodney et al; U.S. Pat. No. 3,911,104, Oct. 7, 1975 to Harrison; U.S. Pat. No. 3,935,306, Jan. 27, 1976 to Roberts et al; and U.S. Pat. No. 4,040,858, Aug. 9, 1977 to Wason.

Application of fluoride ions to dental enamel serves to protect teeth against decay. A wide variety of fluoride ion-yielding materials can be employed as sources of soluble fluoride in the instant electrochemical compositions. Examples of suitable fluoride ion-yielding materials are found in Briner et al; U.S. Pat. No. 3,535,421; issued Oct. 20, 1970 and Widder et al; U.S. Pat. No. 3,678,154; issued Jul. 18, 1972, both patents being incorporated herein by reference. Preferred fluoride ion sources for use herein include stannous fluoride, monofluorophosphate, sodium fluoride, potassium fluoride and ammonium fluoride. Sodium fluoride is particularly preferred. Preferably the instant electrochemical compositions provide from about 50 ppm to 10,000 ppm, more preferably from about 100 to 3000 ppm, of fluoride ions in the aqueous solutions that contact dental surfaces when used with the strip of material used in the mouth. Other anti-caries actives include xylitol.

The electrochemical composition of the present invention may comprise a non-electrochemical antimicrobial agent. Non-electrochemical antimicrobial agents may include, but are not limited to, 5-chloro-2-(2,4-dichlorophenoxy)-phenol, commonly referred to as triclosan, and described in The Merck Index, 11th ed. (1989), pp. 1529 (entry no. 9573) in U.S. Pat. No. 3,506,720, and in European Patent Application No. 0,251,591 of Beecham Group, PLC, published Jan. 7, 1988; phthalic acid and its salts including, but not limited to those disclosed in U.S. Pat. No. 4,994,262, Feb. 19, 1991, substituted monoperthalic acid and its salts and esters as disclosed in U.S. Pat. No. 4,990,329, Feb. 5, 1991, U.S. Pat. No. 5,110,583, May 5, 1992 and U.S. Pat. No. 4,716,035, Dec. 29, 1987, all to Sampathkumar; preferably magnesium monoperoxy phthalate, chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicyanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion actives; antibiotics such as augmentin, amoxicillin, tetracycline, doxycycline, minocycline, and metronidazole; and analogs and salts of the above; essential oils including thymol, geraniol, carvacrol, citral, hinokitiol, eucalyptol, catechol (particularly 4-allyl catechol), metals or metal ions (e.g., silver, copper, zinc, etc) and mixtures thereof; methyl salicylate; chlorite and metal salts of chlorite and mixtures of all of the above.

The electrochemical composition of the present invention may comprise a non-electrochemical anti-inflammatory or non-electrochemical anti-sensitivity agent. Anti-inflammatory agents may include, but are not limited to, non-steroidal anti-inflammatory actives or NSAIDs such as ketorolac, flurbiprofen, ibuprofen, naproxen, indomethacin, aspirin, ketoprofen, piroxicam and meclofenamic acid. Use of NSAIDs such as Ketorolac are claimed in U.S. Pat. No. 5,626,838, issued May 6, 1997, herein incorporated by reference. Disclosed therein are methods of preventing and, or treating primary and reoccurring squamous cell carcinoma of the oral cavity or oropharynx by topical administration to the oral cavity or oropharynx an effective amount of an NSAID.

Anti-sensitivity agents can include potassium nitrate, clove oil (Eugenol) and other herbal or flavor actives/agents.

Nutrients may improve the condition of the oral cavity and can be included in the electrochemical compositions. The electrochemical composition of the present invention may comprise a non-electrochemical nutrient adjunct that may include minerals, vitamins, oral nutritional supplements, enteral nutritional supplements, and mixtures thereof.

Minerals that can be included with the electrochemical compositions of the present invention include calcium, phosphorus, fluoride, zinc, manganese, potassium and mixtures thereof. These minerals are disclosed in Drug Facts and Comparisons (loose leaf drug information service), Wolters Kluer Company, St. Louis, Mo., COPYRIGHT. 1997, pp 10-17; incorporated herein by reference.

Vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Such vitamins are disclosed in Drug Facts and Comparisons (loose leaf drug information service), Wolters Kluer Company, St. Louis, Mo., COPYRIGHT. 1997, pp. 3-10; incorporated herein by reference.

Oral nutritional supplements include amino acids, lipotropics, fish oil, and mixtures thereof, as disclosed in Drug Facts and Comparisons (loose leaf drug information service), Wolters Kluer Company, St. Louis, Mo., COPYRIGHT. 1997, pp. 54-54e; incorporated herein by reference. Amino acids include, but, are not limited to L-Tryptophan, L-Lysine, Methionine, Threonine, Levocamitine or L-carnitine and mixtures thereof. Lipotropics include, but, are not limited to choline, inositol, betaine, linoleic acid, linolenic acid, and mixtures thereof. Fish oil contains large amounts of Omega-3 (N-3) Polyunsaturated fatty acids, eicosapentaenoic acid and docosahexaenoic acid.

Entenal nutritional supplements include, but, are not limited to protein products, glucose polymers, corn oil, safflower oil, medium chain triglycerides as disclosed in Drug Facts and Comparisons (loose leaf drug information service), Wolters Kluer Company, St. Louis, Mo., COPYRIGHT. 1997, pp. 55-57; incorporated herein by reference.

pH Adjustment Agent

Alkaline Material

An alkaline material may be present to trim the pH and/or maintain the pH of the composition according to the present invention. The amount of alkaline material is from about 0.001% to about 20%, preferably from about 0.01% to about 10%, and more preferably from about 0.05% to about 3% by weight of the composition.

Examples of the alkaline material are sodium hydroxide, potassium hydroxide and/or lithium hydroxide, and/or the alkali metal oxide, such as sodium and/or potassium oxide, or mixtures thereof. Preferably, the source of alkalinity is sodium hydroxide or potassium hydroxide, preferably sodium hydroxide.

Acid

The electrochemical composition of the present invention may comprise an acid. Any acid known to those skilled in the art may be used herein. Typically, the composition herein may comprise up to about 20%, preferably from about 0.1% to about 10%, more preferably from about 0.1% to about 5%, even more preferably from about 0.1% to about 3%, by weight of the total composition of an acid.

Suitable acids are selected from the group consisting of a mono- and poly-carboxylic acid or a mixture thereof; a percarboxylic acid or a mixture thereof; a substituted carboxylic acid or a mixture thereof; and mixtures thereof. Carboxylic acids useful herein include $C_{1-6}$ linear or at least about 3 carbon containing cyclic acids. The linear or cyclic carbon-containing chain of the carboxylic acid may be substituted with a substituent group selected from the group consisting of hydroxyl, ester, ether, aliphatic groups having from about 1 to about 6, more preferably from about 1 to about 4 carbon atoms, and mixtures thereof.

Suitable mono- and poly-carboxylic acids are selected from the group consisting of citric acid, lactic acid, ascorbic acid, isoascorbic acid, tartaric acid, formic acid, maleic acid, malic acid, malonic acid, propionic acid, acetic acid, dehydroacetic acid, benzoic acid, hydroxy benzoic acid, and mixtures thereof.

Suitable percarboxylic acids are selected from the group consisting of peracetic acid, percarbonic acid, perboric acid, and mixtures thereof.

Suitable substituted carboxylic acids are selected from the group consisting of an amino acid or a mixture thereof; a halogenated carboxylic acid or a mixture thereof; and mixtures thereof.

Preferred acids for use herein are selected from the group consisting of lactic acid, citric acid, and ascorbic acid and mixtures thereof. More preferred acids for use herein are selected from the group consisting of lactic acid and citric acid and mixtures thereof. An even more preferred acid for use herein is lactic acid.

Suitable acids are commercially available from JBL, T&L, or Sigma. Lactic acid is commercially available from Sigma and Purac.

Methods of Use

The present invention further relates to methods of using the compositions of the present invention to provide disinfecting, cleaning and health benefits.

The present invention further relates to a method for treating wounds comprising contacting the wound in need of treatment with a composition of the present invention and exposing the composition to a current.

The present invention further encompasses a method of disinfecting a surface, the method comprising the steps of contacting the surface with a composition of the present invention and exposing the composition to a current.

The present invention further encompasses a method of removing biofilm from a surface, the method comprising the steps of contacting the biofilm with a composition of the present invention and exposing the composition a current.

The present invention further relates to a method for treating or cleaning the oral cavity, including teeth or dentures (inside or outside the oral cavity), comprising contacting the oral cavity (including teeth or dentures) in need of treatment or cleaning with the electrochemical composition, and exposing the composition to a current.

Packaging

The electrochemical compositions of the present invention may be packed in any suitable packaging for delivering the electrochemical compositions for use. In one preferred aspect, the package may be comprised of polyethylene terephthalate, high-density polyethylene, low-density polyethylene, or combinations thereof. Furthermore, preferably, the package may be dosed through a cap at the top of the package such that the composition exits the bottle through an opening in the cap. In one aspect, the opening in the cap may also contain a screen to help facilitate dosing.

In another aspect, the package may comprise multiple compartments, preferably two compartments, with a first composition in a first compartment and a second composition in a second compartment. It will be understood that the electrochemical mediator and nitrite salt may be included in either or both of the first and second compartments. In one preferred aspect, the first composition may comprise the electrochemical mediator and the second composition may comprise the nitrite salt.

The generation of the gasotransmitters generated from the present invention can be evaluated using an indigo carmine bleaching method.

Indigo Carmine Bleaching Test Method

A solution of the electrochemical mediator is prepared in 1% aqueous aqueous gasotransmitter salt solution containing 2 ppm indigo carmine as a bleaching indicator. A UV/Vis spectra is recorded.

The solution is placed in a cell comprising carbon electrodes and a potentiostat and the potential raised above the redox potential of the mediator. A UV/Vis spectra is recorded after ten minutes. The reduction in the intensity of the indigo carmine visible absorption peak at ~610 nm is used to determine the efficacy of the activator. Activators of the present invention are considered suitable if the Indigo carmine absorption peak intensity was reduced by more than a control solution that does not contain gasotransmitter salt.

Nitric oxide generated from the present invention can be evaluated using a diamino anthraquinone method.

Nitric Oxide Test Method

A solution of the electrochemical mediator is prepared containing 1% of a nitrite or nitrate salt, as described above, and 10 ppm 1,2-diamino anthraquinone in 75/25 v/v water isopropyl alcohol. A UV/Vis spectra is recorded.

The solution is placed in a cell comprising carbon electrodes and a potentiostat and the potential raised above the redox potential of the mediator. A UV/Vis spectra is recorded after ten minutes. The reduction in the intensity of the 1,2-diamino anthraquinone visible absorption peak at 540 nm is used to determine the efficacy of the activator. Activators of the present invention are considered suitable if the absorption peak intensity is reduced by more than a control solution that does not contain nitrite.

Hydrogen Sulfide Test Method

A solution of the electrochemical mediator is prepared containing 1% of a sulfite, sulfate or thiosulfate salt, as described above.

The solution is placed in a cell comprising carbon electrodes and a potentiostat and the potential raised above the redox potential of the mediator. After 10 minutes of electrolysis the solution is tested for hydrogen sulfide using lead acetate paper for example. Activators of the present invention are considered suitable if the test for hydrogen sulfide is positive.

EXAMPLES

The following are non-limiting examples of various compositions of the present invention, and exemplify compositions and methods of their testing and use.

Nitric Oxide Generating Compositions

Topical formulations containing diaminoanthroquinone as an indicator for the formation of nitric oxide are prepared according to Table 1.

TABLE 1

| Ingredient % w/w | A | B | C | D |
| --- | --- | --- | --- | --- |
| Purified Water, USP | 85.0 | 85.0 | 85.0 | 85.0 |
| Sodium Nitrite | 1.0 | 3.0 | 0.5 | 5.0 |
| Benzophenone tetracarboxylic acid | 0.01 | 0.1 | 0.001 | 0.5 |
| Glycerol, NF | 10.0 | 10.0 | 10.0 | 10.0 |
| Diaminoanthroquinone | 0.01 | 0.01 | 0.01 | 0.01 |
| Carbomer Homopolymer Type A, NF Carbopol 974P | 1.0 | 0.3 | — | — |
| Carbomer Interpolymer Type B, NF Carbopol ETD2020NF | — | — | 0.5 | 1.0 |

TABLE 1-continued

| Ingredient % w/w | A | B | C | D |
|---|---|---|---|---|
| Trolamine, NF | To pH 7 | — | | To pH 7 |
| 0.1M Phosphate Buffer | — | To pH 7 | pH 7 | — |
| Purified water USP | To 100 | To 100 | To 100 | To 100 |

The formulations are placed in a cell comprising carbon electrodes and a potentiostat. A potential of 1.3V is applied to the formulations. A UV/Vis spectra is recorded after ten minutes. The reduction in the intensity of the 1,2-diamino anthraquinone visible absorption peak at 540 indicates that nitric oxide is formed.

Hydrogen Sulfide Generating Compositions

Topical formulations are prepared according to Table 2.

TABLE 2

| Ingredient % w/w | A | B | C | D |
|---|---|---|---|---|
| Purified Water, USP | 85.0 | 85.0 | 85.0 | 85.0 |
| Sodium Sulfite | 1.0 | 3.0 | 0.5 | 5.0 |
| Benzophenone tetracarboxylic acid | 0.01 | 0.1 | 0.001 | 0.5 |
| Glycerol, NF | 10.0 | 10.0 | 10.0 | 10.0 |
| Diaminoanthroquinone | 0.01 | 0.01 | 0.01 | 0.01 |
| Carbomer Homopolymer Type A, NF Carbopol 974P | 1.0 | 0.3 | — | — |
| Carbomer Interpolymer Type B, NF Carbopol ETD2020NF | — | — | 0.5 | 1.0 |
| Trolamine, NF | To pH 7 | — | | To pH 7 |
| 0.1M Phosphate Buffer | — | To pH 7 | pH 7 | — |
| Purified water USP | To 100 | To 100 | To 100 | To 100 |

The formulations are placed in a cell comprising carbon electrodes and a potentiostat. A potential of 1.3V is applied to the formulations. Lead acetate paper is contacted with the formulation after ten minutes to indicate the generation of hydrogen sulfide.

Figure 2:
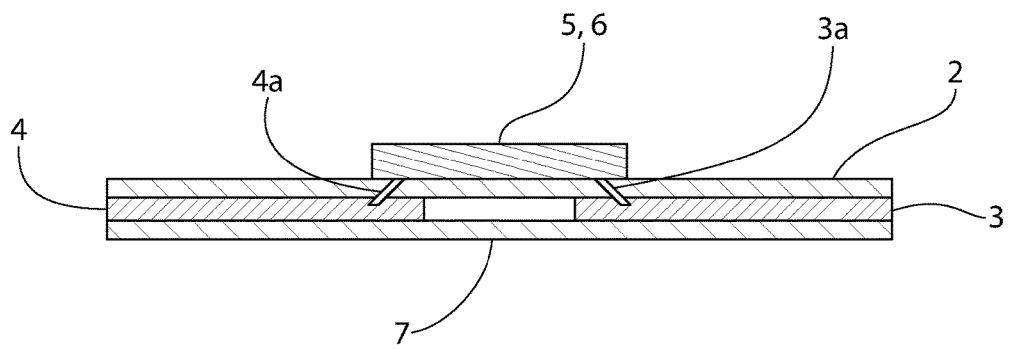
FIG. 2 shows an elevation view schematic of a wound dressing integrating a gasotransmitter composition of matter of the present invention, as well as embodying a gasotransmitter release system of one embodiment of the present invention.
Figure 3:
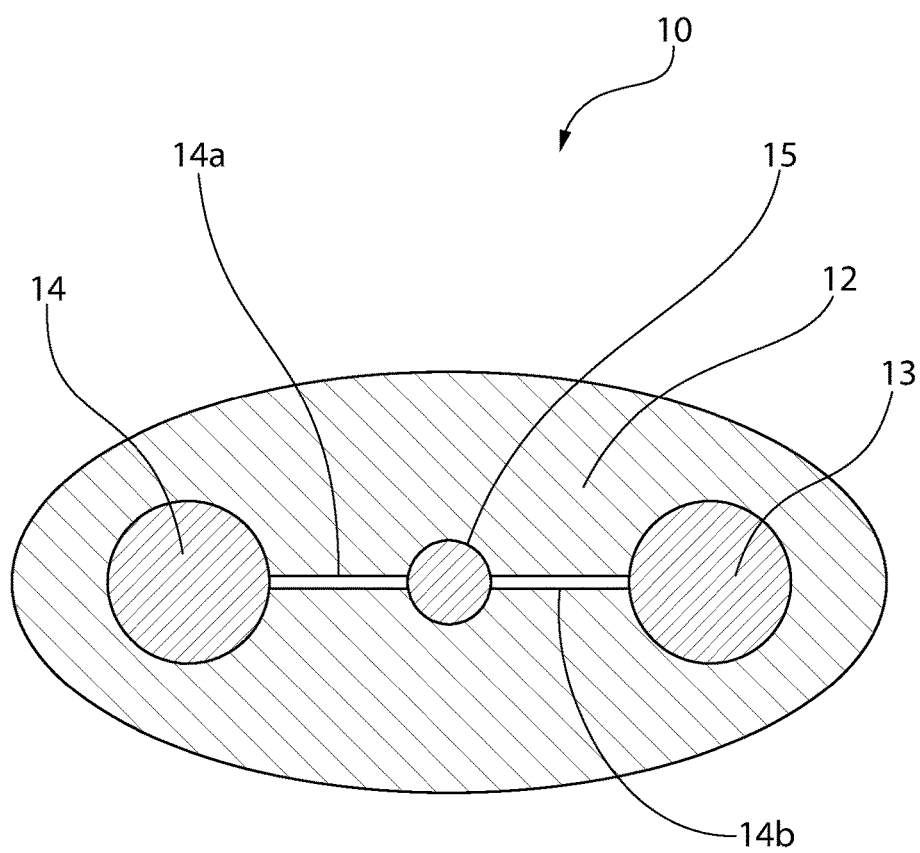
FIG. 3 shows a plan view schematic of a wound dressing integrating a gasotransmitter composition of matter of the present invention, as well as embodying a gasotransmitter release system of another embodiment of the present invention.

As to the bandages or dressings of the present invention, FIGS. 1-3 are general schematics showing the general construction of sample bandages or dressings of the present invention.

FIG. 1 shows a plan view schematic of a wound dressing integrating a gasotransmitter composition of matter of the present invention, as well as embodying a gasotransmitter release system of one embodiment of the present invention.

FIG. 1 shows a schematic of a wound dressing 1 including a wound dressing material 2 supporting anode 3 and cathode 4 which in turn are connected by respective anode electrical connection 3a and cathode electrical connection 4a. Anode 3 and cathode 4 applies a current from battery 5, and controlled by voltage controller 6, to drive the reaction of the gasotransmitter-generating composition of matter to produce a therapeutic gasotransmitter gas, such as nitric oxide (NO) or hydrogen sulfide. In many exemplary embodiments, coin-type batteries may be used.

FIG. 2 shows an elevation view schematic of a wound dressing 1 including a wound dressing material 2 supporting anode 3 and cathode 4 which in turn are connected by respective anode electrical connection 3a and cathode electrical connection 4a. Anode 3 and cathode 4 applies a current from battery 5, and controlled by voltage controller 6, to drive the reaction of the gasotransmitter-generating composition of matter to produce a therapeutic gas, such as nitric oxide (NO) or hydrogen sulfide $H_2S$. FIG. 2 also shows a gasotransmitter layer 7 comprising a carrier material adapted to contain at least one gasotransmitter-generating composition, and to bring it under the effect of a voltage applied by being in electrical contact with the anode 3 and cathode 4 to have its electrolytic reaction driven thereby.

The aqueous solution, emulsion, solid, gel, hydrogel, organogel, or film, or combination of an aqueous solution composition and a material, such as a film, may be incorporated into a carrier material.

The carrier material may be any material or combination of materials effective to contain and preserve the gasotransmitter-generating composition(s), such as a bandage, gauze, foam, sponge, hydrogel, hydrocolloid, hydrofiber, occlusive dressing, adhesive composition or scaffold, which can be positioned at a wound or other therapeutic site so as to bring to bear a therapeutically effective amount and concentration of the gasotransmitter(s).

The dimensions of the bandage or dressing (such as size, shape and thickness) as well as the type of materials used to contain the electrolytic reaction components and associated carrier may be selected in accordance with the desired exposure of the targeted site to the gasotransmitter generating composition, as will be appreciated by one of ordinary skill in the fields of pharmacokinetics and medicine.

In some embodiments, the dressing or bandage may be constructed with regard for the need to provide a sufficient gasotransmitter to effectively allow for the diffusion of the gasotransmitter into the tissue at the target site over time, such that the amount and rate of the release of gasotransmitters is regulated accordingly either by adjusting the amount and/or formulation of the gasotransmitter-generating composition(s) and/or the applied current driving the electrolytic reaction.

In some embodiments the dressing or bandage may be constructed so as to maintain sufficient gasotransmitters at the target site over time by incorporating appropriate adhesives into the dressing or bandage in topical applications, so as to effectively hold the gasotransmitter(s) in therapeutic contact with the target tissue site, to permit diffusion into the tissue surface.

FIG. 3 shows a plan view schematic of a wound dressing integrating a gasotransmitter composition of matter of the present invention, as well as embodying a gasotransmitter release system of another embodiment of the present invention.

FIG. 3 shows a schematic of a wound dressing 11 including a wound dressing material 12 supporting anode 13 and cathode 14 which in turn are connected by respective anode electrical connection 13a and cathode electrical connection 14a. Anode 13 and cathode 14 applies a current from connector 15 that is connected to an external power source (not depicted) to drive the reaction of the gasotransmitter-generating composition of matter to produce a therapeutic gas, such as nitric oxide (NO) or hydrogen sulfide. The external power source may include a voltage controller.

It will be appreciated that the dressings of the present invention may be incorporated into, and bandages of the present invention may be in any form of, bandages in accordance with known designs and manufacture, including adhesive bandages, including those that may be provided with adhesive surrounding areas of the target site and that are adapted to form a vapor barrier around the target site area, to best bring to application the gasotransmitter(s).

Figure 4:
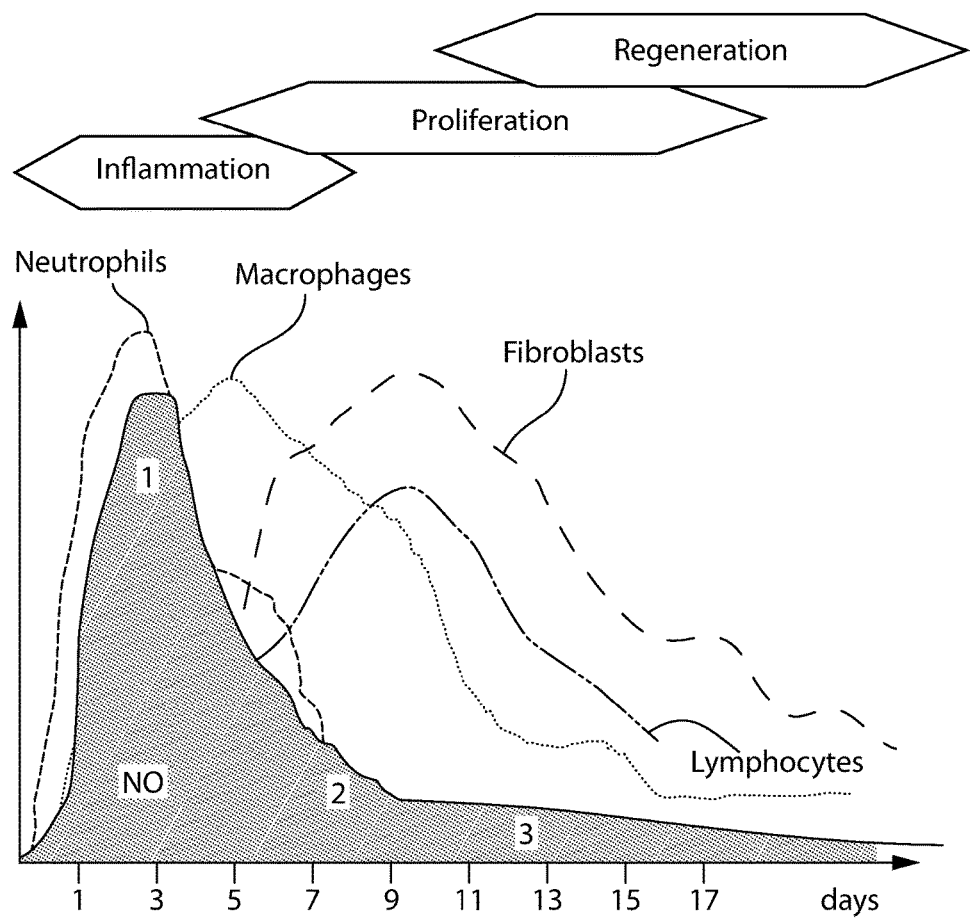
FIG. 4 is a graph of nitric oxide (NO) over time showing the use of nitirc oxide through the several stages of human wound healing.

FIG. 4 is a graph of nitric oxide over time showing that the human body is adept at utilizing nitric oxide through the several stages of wound healing among several different cell types.

The present invention also includes a means for controlling the gasotransmitter levels at the applied site, area or volume through active control of the applied current and/or voltage to the electrolytic reaction.

Figure 5:
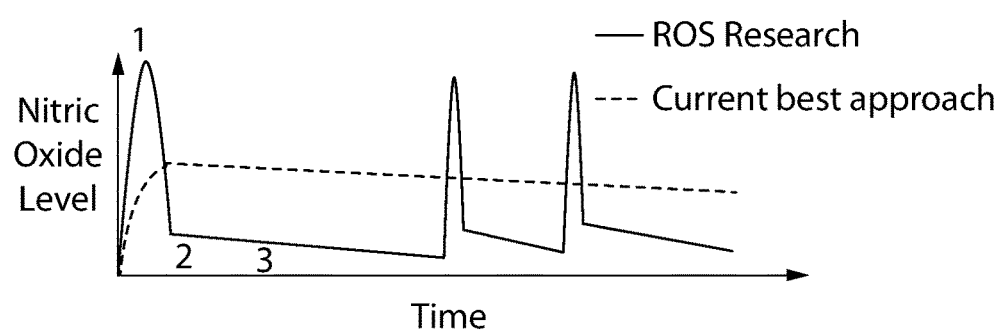
FIG. 5 is a graph of nitric oxide (NO) over time showing the variation in applied nitric oxide levels at a wound site in accordance with one embodiment of the method of the present invention.

FIG. 5 is a graph of nitric oxide (NO) over time showing an example of the variation in applied nitric oxide levels at a wound site in accordance with one embodiment of the method of the present invention. This graph shows that the nitric oxide level is relatively high during the wound disinfection stage, relatively lower during the initiation of tissue regeneration, and lowest during the completion of healing; and this varies temporally across the various cell types. Accordingly, the present invention allows for the variation of the dispensation and application of a gasotransmitter over a therapeutic period so as to bring about a more efficient use of a gasotransmitter over that therapeutic period. This may be brought about by microprocessor control over the amount, timing and duration of current application to the electrolytic cell. Accordingly, the present invention may include an optional control microprocessor that may exert control over the battery or the external power source. The microprocessor may be programmed to include a clock function as well as a voltage controller to control the application of current to the electrolytic cell. FIG. 5 shows several regions (such as peaks 1 and others) and regions 2 and 3 of a lower level of gasotransmitter (nitric oxide) generation that may be brought about through the microprocessor controller so as to provide regulated delivery. The nitric oxide generation profile may be varied or repeated through two or more cycles and/or at two or more sites.

The control microprocessor may also be used to vary the application of a gasotransmitter spatially either as regards areas of a single dressing or among several contemporaneously applied dressings.

Figure 6:
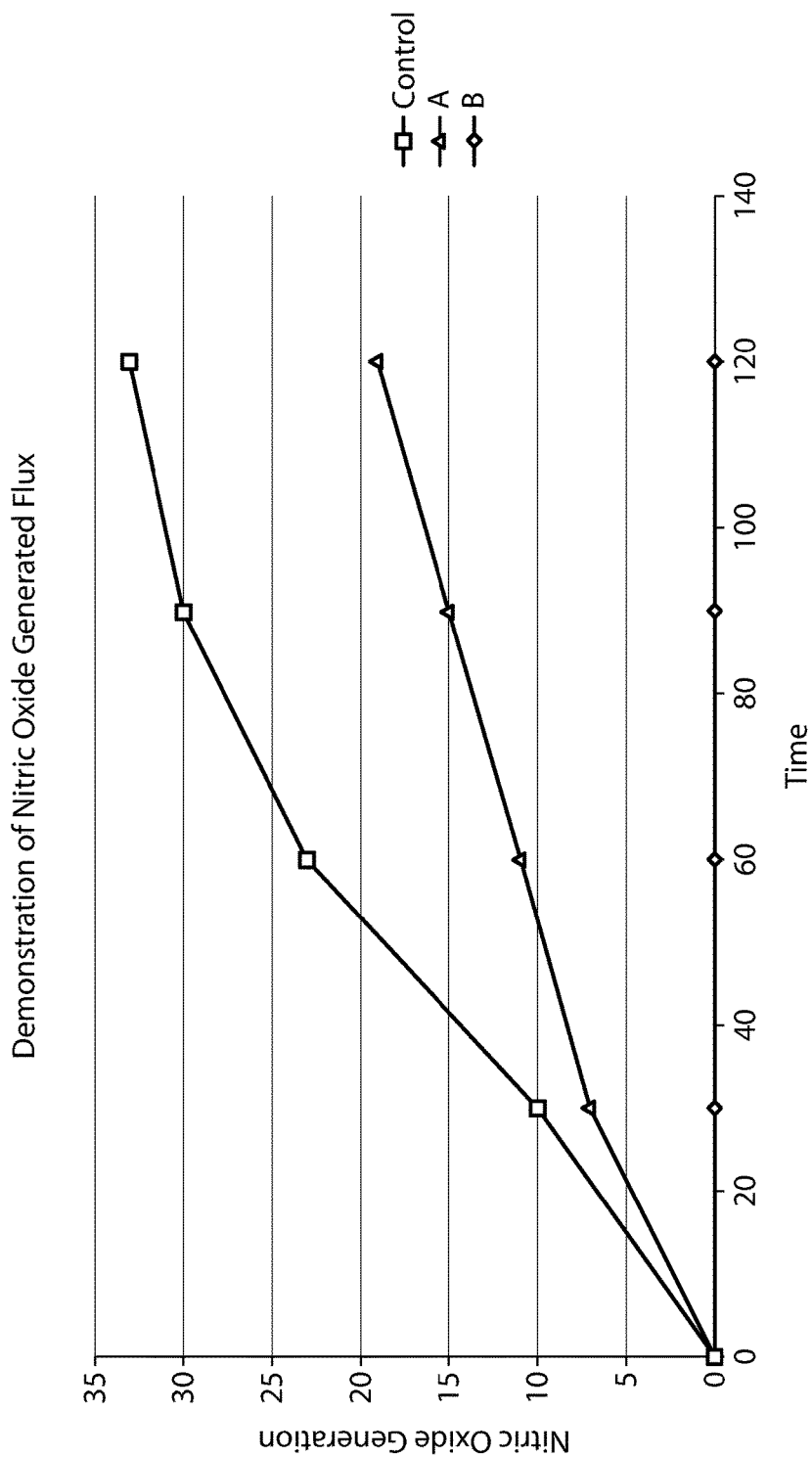
FIG. 6 is a graph of nitric oxide (NO) over time showing the variation nitric oxide generation at a wound site, demonstrating discrete, real-time control of nitric oxide production/concentration in accordance with one embodiment of the method of the present invention.

FIG. 6 is a graph of nitric oxide (NO) over time showing the variation nitric oxide generation at a wound site, demonstrating discrete, real-time control of nitric oxide production/concentration in accordance with one embodiment of the method of the present invention. This graph elucidates the variable control of nitric oxide concentration permitting discrete spatial and/or temporal real-time control of nitirc oxide production and associated therapeutic effect.

The electronic reaction-driving portions of the dressing or bandage may be selected in accordance with spatial and other practical requirements in terms of whether on-board battery or an external power source may be used, as well as with due regard to the amount of current that may be required over the anticipated therapeutic time frame of gasotransmitter application. In some dressings or bandages, the amount and rate of the release of gasotransmitters may be regulated by adjusting the amount and/or formulation of the gasotransmitter-generating composition(s) as well as through the active control of the applied current and/or voltage to the electrolytic reaction over time.

The present invention further includes a method of treating a variety of trauma and disease states by applying a therapeutically effective amount of at least one gasotransmitter thereto. This is done by bringing a composition according to the present invention into therapeutic proximity (meaning within sufficient proximity to be able to effectively dose the gasotransmitter generated from electrolytic reaction involving the gasotransmitter-generating compositions) with a disease-affected or traumatized tissue, exposing the composition to a voltage. The therapeutic methods of the present invention may be practiced through use of the dressings or bandages of the present invention, or through other arrangements whereby the composition according to the present invention is brought into therapeutic proximity with a disease-affected or traumatized tissue, and then exposed to a voltage.

Such methods include generally a method of treating a wound at a wound target site, the method comprising the steps of: (a) bringing the wound target site in therapeutic proximity with a composition according to any one of the preceding claims; and (b) exposing the composition to a voltage.

The present invention may also be applied to treat a wide variety of disease states. Among these are included a method of treating acne vulgaris at an acne-vulgaris-affected target site, the method comprising the steps of: (a) bringing the acne-vulgaris-affected target site in therapeutic proximity with a composition according to any one of the preceding claims; and (b) exposing the composition to a voltage.

The present invention also includes a method of treating skin ulcers at an ulcerated target site, the method comprising the steps of: (a) bringing the ulcerated target site in therapeutic proximity with a composition according to any one of the preceding claims; and (b) exposing the composition to a voltage.

The present invention further includes method of treating a virus, the method comprising the steps of: (a) bringing the virus in therapeutic proximity with a composition according to any one of the preceding claims; and (b) exposing the composition to a voltage.

It should be understood that every maximum numerical limitation given throughout this specification would include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

REFERENCES

1. Wang, R. Gasotransmitters: growing pains and joys. Trends Biochem. Sci. 39, 227-32 (2014).
2. Mustafa, A. K., Gadalla, M. M. & Snyder, S. H. Signaling by gasotransmitters. Sci. Signal. 2, re2 (2009).
3. Richter-Addo, G. B., Legzdins, P. & Burstyn, J. Introduction: Nitric Oxide Chemistry. Chem. Rev. 102, 857-860 (2002).

4. Tinajero-Trejo, M., Jesse, H. E. & Poole, R. K. Gasotransmitters, poisons, and antimicrobials: it's a gas, gas, gas! F1000Prime Rep. 5, 28 (2013).

5. Agrawal, R. P. et al. A Clinical Trial of Nitrosense patch for the treatment of patients with painful diabetic neuropathy. The Journal of the Association of Physicians of India 62, 385-90 (2014).

6. Yuen, K. C. J., Baker, N. R. & Rayman, G. Treatment of Chronic Painful Diabetic Neuropathy With Isosorbide Dinitrate Spray: A double-blind placebo-controlled crossover study. Diabetes Care 25, 1699-1703 (2002).

7. SMITH, D. J., Lopez, M. & LOPEZ-JARAMILLO, P. TOPICAL NITRIC OXIDE DONOR DEVICES. (2006).

8. Kida, K., Marutani, E., Nguyen, R. K. & Ichinose, F. Inhaled hydrogen sulfide prevents neuropathic pain after peripheral nerve injury in mice. Nitric Oxide 46, 87-92 (2015).

9. Jung, J. & Jeong, N. Y. Hydrogen sulfide controls peripheral nerve degeneration and regeneration: a novel therapeutic strategy for peripheral demyelinating disorders or nerve degenerative diseases. Neural Regen. Res. 9, 2119-21 (2014).

10. Jian-qing Lin, Hui-qin Luo, Cai-zhu Lin, Jin-zhuan Chen, and X. L. Sodium Hydrosulfide Relieves Neuropathic Pain in Chronic Constriction Injured Rats. Evidence-Based Complement. Altern. Med. (2014). doi:doi:10.1155/2014/514898

11. Organ and tissue preservation cold storage solution. (2002).

12. Pinsky, D. J. et al. The nitric oxide/cyclic GMP pathway in organ transplantation: critical role in successful lung preservation. Proc. Natl. Acad. Sci. U.S.A. 91, 12086-90 (1994).

13. Use of nitric oxide or nitric oxide adducts to preserve platelets. (1996).

14. Store donated blood for more than three weeks? Say NO (nitric oxide) |Emory University |Atlanta, GA.

15. Chen, E. P. et al. The controlled delivery of hydrogen sulfide for the preservation of heart tissue. (2011).

16. Hosgood, S. A. & Nicholson, M. L. Hydrogen sulphide ameliorates ischaemia-reperfusion injury in an experimental model of non-heart-beating donor kidney transplantation. Br. J. Surg. 97, 202-9 (2010).

17. Xie, X. et al. Transplantation of mesenchymal stem cells preconditioned with hydrogen sulfide enhances repair of myocardial infarction in rats. Tohoku J. Exp. Med. 226, 29-36 (2012).

18. Emerson, M. Hydrogen Sulfide and Platelets: A Possible Role in Thrombosis. Handb. Exp. Pharmacol. 230, 153-62 (2015).

19. Elrod, J. W. et al. Hydrogen sulfide attenuates myocardial ischemia-reperfusion injury by preservation of mitochondrial function. Proc. Natl. Acad. Sci. U.S.A. 104, 15560-5 (2007).

20. Zagli, G. et al. Hydrogen sulfide inhibits human platelet aggregation. Eur. J. Pharmacol. 559, 65-8 (2007).

21. Wang, G. et al. Hydrogen sulfide accelerates wound healing in diabetic rats. Int. J. Clin. Exp. Pathol. 8, 5097-104 (2015).

22. Luo, J., Chen, A. F. & Chen P, A. F. Nitric oxide: a newly discovered function on wound healing. Acta Pharmacol. Sin. 26, 259-264 (2005).

23. Schulz, G. & Stechmiller, J. Wound healing and nitric oxide production: too little or too much may impair healing and cause chronic wounds. Int. J. Low. Extrem. Wounds 5, 6-8 (2006).

24. Schwentker, A. & Billiar, T. R. Nitric oxide and wound repair. Surg. Clin. North Am. 83, 521-30 (2003).

25. Papapetropoulos, A. et al. Hydrogen sulfide is an endogenous stimulator of angiogenesis. Proc. Natl. Acad. Sci. U.S.A. 106, 21972-7 (2009).

26. Adler, B. L. & Friedman, A. J. Nitric oxide therapy for dermatologic disease. Future Science OA 1, (2015).

27. Neidrauer, M. et al. Antimicrobial efficacy and wound-healing property of a topical ointment containing nitric-oxide-loaded zeolites. J. Med. Microbiol. 63, 203-209 (2014).

28. Miller, C. et al. Gaseous nitric oxide bactericidal activity retained during intermittent high-dose short duration exposure. Nitric Oxide—Biol. Chem. 20, 16-23 (2009).

29. Sulemankhil, I. et al. Prevention and treatment of virulent bacterial biofilms with an enzymatic nitric oxide-releasing dressing. Antimicrob. Agents Chemother. 56, 6095-103 (2012).

What is claimed is:

1. A therapeutic dressing comprising:
   (a) a composition comprising:
      (i) an organic electrochemical mediator configured to reduce a gasotransmitter salt; and
      (ii) the gasotransmitter salt converting into a gasotransmitter upon reduction;
   (b) a carrier adapted to contain said composition; and
   (c) a source of current in electrical contact with said composition capable of producing the gasotransmitter.

2. The therapeutic dressing according to claim 1 wherein the gasotransmitter salt is selected from nitrate, nitrite, sulfate, thiosulfate and sulfite salts.

3. The therapeutic dressing according to claim 2, wherein said gasotransmitter salt is a nitrite salt, and where said nitrite salt is selected from the group consisting of nitrite salts of sodium, potassium, calcium and magnesium.

4. The therapeutic dressing according to claim 2, wherein said gasotransmitter salt is a sulfite salt, and wherein said sulfite salt is selected from the group consisting of sulfite salts of sodium, potassium, calcium and magnesium.

5. The therapeutic dressing according to claim 1 wherein the electrochemical mediator has a reduction potential of from about −0.1 V to about −2.0 V.

6. The therapeutic dressing according to claim 1 wherein the electrochemical mediator has a reduction potential of from about −0.5 V to about −1.7 V.

7. The therapeutic dressing according to claim 1 wherein the electrochemical mediator has a reduction potential of from about −0.75 V to about −1.5 V.

8. The therapeutic dressing according to claim 1, wherein the electrochemical mediator is selected from the group consisting of benzophenones, quinones, and derivatives thereof.

9. The therapeutic dressing according to claim 8 wherein said electrochemical mediator comprises a redox moiety and a hydrophilic moiety selected from the group consisting of alcohol, amine, amide, carboxylic acid, sulfonic acid and phosphatealkylene oxide oligomers, alkylene oxide polymers, alkylene oxide copolymers, ethylene glycol, vinyl alcohol, vinyl pyrrolidone, acrylic acid, methacrylic acid, acrylamide, cellulose, carboxymethyl cellulose, chitosan, dextran, 2-ethyl-2-oxazoline, hydroxyethyl methacrylate, vinyl pyridine-N-oxide, diallyl dimethyl ammonium chloride, maleic acid, lysine, isopropyl acrylamide, styrene sulfonic acid, vinyl methyl ether, vinyl phosphonic acid, ethylene imine, and mixtures thereof.

10. The therapeutic dressing according to claim 1, wherein the electrochemical mediator is selected from the group consisting of fluorescein, xanthone, thioxanthone, and derivatives thereof.

11. The therapeutic dressing according to claim 10 wherein said electrochemical mediator comprises a redox moiety and a hydrophilic moiety selected from the group consisting of alcohol, amine, amide, carboxylic acid, sulfonic acid and phosphatealkylene oxide oligomers, alkylene oxide polymers, alkylene oxide copolymers, ethylene glycol, vinyl alcohol, vinyl pyrrolidone, acrylic acid, methacrylic acid, acrylamide, cellulose, carboxymethyl cellulose, chitosan, dextran, 2-ethyl-2-oxazoline, hydroxyethyl methacrylate, vinyl pyridine-N-oxide, diallyl dimethyl ammonium chloride, maleic acid, lysine, isopropyl acrylamide, styrene sulfonic acid, vinyl methyl ether, vinyl phosphonic acid, ethylene imine, and mixtures thereof.

12. The therapeutic dressing according to claim 1, wherein said gasotransmitter salt comprises
a nitrite or nitrate salt which converts into a nitric oxide via electron transfer.

13. The therapeutic dressing according to claim 12 wherein said gasotransmitter salt comprises
the nitrite salt having the formula:

$$A[NO2]_m$$

wherein
A is selected from the group consisting of monovalent cations, divalent cations, and trivalent cations selected from the group consisting of aluminum, barium, calcium, cobalt, chromium, copper, iron, lithium, potassium, rubidium, magnesium, manganese, molybdenum, nickel, sodium, titanium, vanadium, zinc, ammonium, alkyl-ammonium, and aryl-ammonium cations, and mixtures thereof.

14. The therapeutic dressing according to claim 12 wherein said nitrate or nitrite salt has a cation consisting of monovalent cations, divalent cations, and trivalent cations selected from the group consisting of aluminum, barium, calcium, cobalt, chromium, copper, iron, lithium, potassium, rubidium, magnesium, manganese, molybdenum, nickel, sodium, titanium , vanadium, and zinc cations, or mixtures thereof.

15. The therapeutic dressing according to claim 1 wherein said gasotransmitter salt comprises
a sulfite, sulfate or thiosulfate salt which converts into a hydrogen sulfide via electron transfer.

16. The therapeutic dressing according to claim 15 wherein said gasotransmitter salt comprises
the sulfite salt having the formula:

$$A_n[SO_3]_m$$

wherein
A is selected from the group consisting of monovalent cations, divalent cations, and trivalent cations selected from the group consisting of aluminum, barium, calcium, cobalt, chromium, copper, iron, lithium, potassium, rubidium, magnesium, manganese, molybdenum, nickel, sodium, titanium , vanadium, zinc, ammonium, alkyl-ammonium, and aryl-ammonium cations, and mixtures thereof.

17. The therapeutic dressing according to claim 15 wherein said sulfate, thiosulfate or sulfite salt has a cation consisting of monovalent cations, divalent cations, and trivalent cations selected from the group consisting of aluminum, barium, calcium, cobalt, chromium, copper, iron, lithium, potassium, rubidium, magnesium, manganese, molybdenum, nickel, sodium, titanium, vanadium, and zinc cations, and mixtures thereof.

18. The therapeutic dressing according to claim 1, wherein said electrochemical mediator is a water soluble ketone or derivative thereof.

19. The therapeutic dressing according to claim 18 wherein said electrochemical mediator comprises a redox moiety and a hydrophilic moiety selected from the group consisting of alcohol, amine, amide, carboxylic acid, sulfonic acid and phosphatealkylene oxide oligomers, alkylene oxide polymers, alkylene oxide copolymers, ethylene glycol, vinyl alcohol, vinyl pyrrolidone, acrylic acid, methacrylic acid, acrylamide, cellulose, carboxymethyl cellulose, chitosan, dextran, 2-ethyl-2-oxazoline, hydroxyethyl methacrylate, vinyl pyridine-N-oxide, diallyl dimethyl ammonium chloride, maleic acid, lysine, isopropyl acrylamide, styrene sulfonic acid, vinyl methyl ether, vinyl phosphonic acid, ethylene imine, and mixtures thereof.

20. A bandage comprising the therapeutic dressing according to claim 1, wherein said bandage is constructed to maintain the dressing at a target site of a patient.

21. The bandage according to claim 20, additionally comprising a voltage controller controlling a current from said source of current.

* * * * *